US012661397B2

(12) United States Patent
Jia et al.

(10) Patent No.: US 12,661,397 B2
(45) Date of Patent: Jun. 23, 2026

(54) ADJUVANT COMPRISING A GLYCOARCHAEOL AND AN IMMUNOSTIMULANT

(71) Applicant: NATIONAL RESEARCH COUNCIL OF CANADA, Ottawa (CA)

(72) Inventors: Yimei Jia, Nepean (CA); Michael Mccluskie, Ottawa (CA); Bassel Akache, Ottawa (CA); Lakshmi Krishnan, Ottawa (CA)

(73) Assignee: NATIONAL RESEARCH COUNCIL OF CANADA, Ottawa (CA)

( * ) Notice: Subject to any disclaimer, the term of this patent is extended or adjusted under 35 U.S.C. 154(b) by 388 days.

(21) Appl. No.: 18/260,133

(22) PCT Filed: Jan. 5, 2022

(86) PCT No.: PCT/IB2022/050067
§ 371 (c)(1),
(2) Date: Jun. 30, 2023

(87) PCT Pub. No.: WO2022/149074
PCT Pub. Date: Jul. 14, 2022

(65) Prior Publication Data

US 2024/0082391 A1 Mar. 14, 2024

Related U.S. Application Data

(60) Provisional application No. 63/134,251, filed on Jan. 6, 2021.

(51) Int. Cl.
*A61K 39/39* (2006.01)
*A61K 39/00* (2006.01)
*A61K 39/215* (2006.01)
*A61P 35/00* (2006.01)
*A61P 37/04* (2006.01)

(52) U.S. Cl.
CPC .......... *A61K 39/39* (2013.01); *A61K 39/0011* (2013.01); *A61K 39/001156* (2018.08); *A61K 39/00119* (2018.08); *A61K 39/215* (2013.01); *A61P 35/00* (2018.01); *A61P 37/04* (2018.01); *A61K 2039/55511* (2013.01); *A61K 2039/55555* (2013.01); *A61K 2039/55561* (2013.01); *A61K 2039/55572* (2013.01); *A61K 2039/55577* (2013.01); *A61K 2039/572* (2013.01); *A61K 2039/575* (2013.01)

(58) Field of Classification Search
None
See application file for complete search history.

(56) References Cited

FOREIGN PATENT DOCUMENTS

WO 2016/004512 A1 1/2016

OTHER PUBLICATIONS

Akache et al. Sulfated lactosyl archaeol (SLA) archaeosomes as a vaccine adjuvant. Hum Vaccin Immunother. Dec. 31, 2024;20(1): 2395081. doi: 0.1080/21645515.2024.2395081. Epub Sep. 15, 2024.*
Elmowalid et al. Proc. Natl. Acad. Sci. U.S.A. 104 (20) 8427-8432, (2007).*
International Search Report issued in PCT/IB2022/050067, dated May 9, 2022.
Akache et al., "Effect of Different Adjuvants on the Longevity and Strength of Humoral and Cellular Immune Responses to the HCV Envelope Glycoproteins," Vaccines 7:204 (2019).
Akache et al., "Generation of a Liposomal Vaccine Adjuvant Based on Sulfated S-Lactosylarchaeol (SLA) Glycolipids." In: Thomas, S. (eds) Vaccine Design. Methods in Molecular Biology, 2412: 255-67. Humana, New York, NY (2021).
Akache et al., "Immunogenic and efficacious SARS-CoV-2 vaccine based on resistin-trimerized spike antigen SmT1 and SLA archaeosome adjuvant," Sci Rep 11:21849 (2021).
Akache et al., "Sulfated Lactosyl Archaeol Archaeosomes Synergize with Poly(I:C) to Enhance the Immunogenicity and Efficacy of a Synthetic Long Peptide-Based Vaccine in a Melanoma Tumor Model," Pharmaceutics13(2): 257 (2021).
Alving et al., "Adjuvants for human vaccines," Curr Opin Immunol 24(3):310-5 (2012).
Haq et al., "Archaeal lipid vaccine adjuvants for induction of cell-mediated immunity," Expert Rev Vaccines 15(12):1557-66 (2016).
Jia et al., "A comparison of the immune responses induced by antigens in three different archaeosome-based vaccine formulations," Int J Pharm 561:187-96 (2019).
Jia et al., "The Synergistic Effects of Sulfated Lactosyl Archaeol Archaeosomes When Combined with Different Adjuvants in a Murine Model," Pharmaceutics 13(2):205 (2021).
Mccluskie et al., "Sulfated archaeal glycolipid archaeosomes as a safe and effective vaccine adjuvant for induction of cell-mediated immunity," Hum Vaccine & Immunotherapeutics 13(12):2772-9 (2017).
Mohammad et al., "TLR Agonist Augments Prophylactic Potential of Acid Inducible Antigen Rv3203 against *Mycobacterium tuberculosis* H37Rv in Experimental Animals," PLoS One 11(3):e0152240 (2016).
Van Hoeven et al., "A combination of TLR-4 agonist and saponin adjuvants increases antibody diversity and protective efficacy of a recombinant West Nile Virus antigen," npj Vaccines 3:39 (2018).

* cited by examiner

*Primary Examiner* — Oluwatosin A Ogunbiyi
(74) *Attorney, Agent, or Firm* — MEDLER FERRO WOODHOUSE & MILLS PLLC

(57) ABSTRACT

Provided is an adjuvant composition comprising a glycoarchaeol and at least one immunostimulant selected from a Toll-like receptor (TLR) agonist and a saponin. The glycoarchaeol and/or immunostimulant may be present as a pharmaceutically acceptable salt. The adjuvant composition may be comprised together with an antigen in an immunogenic composition, such as a vaccine composition, which may be for use to induce an immune response in a subject. Further provided is use of the immunogenic composition to induce an immune response in a subject, particularly an immune response that comprises both a cell-mediated response and a humoral response.

19 Claims, 10 Drawing Sheets

Specification includes a Sequence Listing.

SEQUENCE LISTING

```
<160> NUMBER OF SEQ ID NOS: 11

<210> SEQ ID NO 1
<211> LENGTH: 25
<212> TYPE: PRT
<213> ORGANISM: Gallus gallus

<400> SEQUENCE: 1

Leu Glu Gln Leu Glu Ser Ile Ile Asn Phe Glu Lys Leu Thr Glu Trp
1               5                   10                  15

Thr Ser Ser Asn Val Met Glu Glu Arg
            20                  25


<210> SEQ ID NO 2
<211> LENGTH: 24
<212> TYPE: PRT
<213> ORGANISM: Mus musculus

<400> SEQUENCE: 2

Val Thr Asn Thr Glu Met Phe Val Thr Ala Pro Asp Asn Leu Gly Tyr
1               5                   10                  15

Met Tyr Glu Val Gln Trp Pro Gly
            20


<210> SEQ ID NO 3
<211> LENGTH: 25
<212> TYPE: PRT
<213> ORGANISM: Mus musculus

<400> SEQUENCE: 3

Ala Leu Leu Ala Val Gly Ala Leu Glu Gly Pro Arg Asn Gln Asp Trp
1               5                   10                  15

Leu Gly Val Pro Arg Gln Leu Val Thr
            20                  25


<210> SEQ ID NO 4
<211> LENGTH: 25
<212> TYPE: PRT
<213> ORGANISM: Mus musculus

<400> SEQUENCE: 4

Thr Gln Pro Gln Ile Ala Asn Cys Ser Val Tyr Asp Phe Phe Val Trp
1               5                   10                  15
```

-continued

Leu His Tyr Tyr Ser Val Arg Asp Thr
            20                  25

<210> SEQ ID NO 5
<211> LENGTH: 12
<212> TYPE: PRT
<213> ORGANISM: Hepatitis B virus

<400> SEQUENCE: 5

Ile Pro Gln Ser Leu Asp Ser Trp Trp Thr Ser Leu
1               5                   10

<210> SEQ ID NO 6
<211> LENGTH: 8
<212> TYPE: PRT
<213> ORGANISM: Gallus gallus

<400> SEQUENCE: 6

Ser Ile Ile Asn Phe Glu Lys Leu
1               5

<210> SEQ ID NO 7
<211> LENGTH: 17
<212> TYPE: PRT
<213> ORGANISM: Gallus gallus

<400> SEQUENCE: 7

Ile Ser Gln Ala Val His Ala Ala His Ala Glu Ile Asn Glu Ala Gly
1               5                   10                  15

Arg

<210> SEQ ID NO 8
<211> LENGTH: 12
<212> TYPE: PRT
<213> ORGANISM: Gallus gallus

<400> SEQUENCE: 8

Thr Glu Trp Thr Ser Ser Asn Val Met Glu Glu Arg
1               5                   10

<210> SEQ ID NO 9
<211> LENGTH: 9
<212> TYPE: PRT
<213> ORGANISM: Mus musculus

<400> SEQUENCE: 9

Thr Ala Pro Asp Asn Leu Gly Tyr Met
1               5

<210> SEQ ID NO 10
<211> LENGTH: 9
<212> TYPE: PRT
<213> ORGANISM: Mus musculus

<400> SEQUENCE: 10

Glu Gly Pro Arg Asn Gln Asp Trp Leu
1               5

<210> SEQ ID NO 11
<211> LENGTH: 9
<212> TYPE: PRT

-continued

<213> ORGANISM: Mus musculus

<400> SEQUENCE: 11

Ser Val Tyr Asp Phe Phe Val Trp Leu
1 5

ADJUVANT COMPRISING A GLYCOARCHAEOL AND AN IMMUNOSTIMULANT

FIELD

The present application relates generally to the field of immunology and more particularly to adjuvants for use in immunogenic compositions, such as vaccines.

BACKGROUND

Vaccines are biological preparations that improve immunity to a particular disease. They are frequently used in the prophylaxis of humans and animals to protect against infectious diseases caused by bacteria, viruses and parasitic organisms. Vaccines are also under investigation for other therapeutic applications, such as cancer treatment.

The antigens used in vaccines may include a variety of agents, such as killed pathogenic organisms, pathogenic organisms that are alive but modified or attenuated, nucleic acids coding for proteins, purified or recombinant proteins or fragments thereof. It is also often necessary to add an adjuvant to enhance the host immune response to the antigen, and in some cases slow the release of the antigen from the injection site. Adjuvants are substances that can enhance the response to a vaccine and can act in many different ways such as providing a depot effect or inducing immunostimulation.

A wide range of adjuvants have been studied for use in vaccines. Adjuvants currently approved for used in human vaccines include aluminum salts such as aluminum hydroxide, aluminum phosphate, and aluminum potassium sulfate (alum); CpG oligodeoxynucleotides (CpG ODN); oil-in-water emulsions (such as MF59 and AS03), AS04 (3'-O-deacylated monophosphoryl lipid A (MPL) plus aluminum salts), and AS01 (MPL and saponin QS-21 formulated in liposomes), with aluminum salts being the most commonly used.

Archaeosomes are lipid vesicles (liposomes) that are typically comprised of total polar lipids or semi-synthetic glycolipids of ether-linked isoprenoid phytanyl cores with varied glyco- and amino head groups that possess strong adjuvant and immunostimulatory properties. One archaeosome formulation comprises a sulfated disaccharide group covalently linked to the free sn-1 hydroxyl backbone of an archaeal core moiety (SLA; 6'-sulfate-β-D-Galp-(1,4)-β-D-Glcp-(1,1)-archaeol) (see McCluskie et al, 2017, Akache et al, 2018, and WO 2016/004512; the contents of each of which are hereby incorporated by reference in their entirety). McCluskie et al (2017), Akache et al (2018), and WO 2016/004512 have shown that archaeosomes comprising SLA, either individually or mixed with an uncharged glycolipid (e.g. lactosylarchaeol, LA), induce strong antigen-specific IgG and CD8 T cell responses to entrapped antigens and induce the expression of a number of cytokines/chemokines including IL-6, G-CSF, KC and MIP-2. Jia et al (2019, 2020), Akache et al (2019), Agbayani et al (2020) and Stark et al (2019) have also shown that archaeosomes comprising SLA can induce strong antigen-specific immune responses when simply admixed with antigen, as well as in an entrapped formulation.

Adjuvants can enhance and often re-direct the immune response to vaccine antigens, or alternatively provide a carrier effect for an antigen (depot) to be retained for longer periods at the injection site or neighboring lymph nodes. The main immune response mechanisms are the induction of neutralizing antibodies (humoral response) and the generation of T cells (cell-mediated response), including CD4+ helper (Th) and CD8+ cytotoxic (cytotoxic T-lymphocyte) responses. The success of a vaccine depends on its ability to evoke a strong and/or long-lasting and appropriate immune response. Different adjuvants evoke distinct immune responses. For example, aluminum salts evoke a strong humoral response, but only a weak cell-mediated response. Aluminum salts are not able to elicit the strong cell-mediated immune responses required to treat chronic viral infections and cancer.

There is significant demand for adjuvants that are able to rapidly induce strong, effective, and long-lasting immune responses.

SUMMARY

According to a first aspect there is provided an adjuvant composition comprising:

- a glycoarchaeol or a pharmaceutically acceptable salt thereof, and at least one immunostimulant selected from a Toll-like receptor (TLR) agonist or a pharmaceutically acceptable salt thereof and a saponin or a pharmaceutically acceptable salt thereof.

In an embodiment the glycoarchaeol comprises an archaeol core moiety.

In an embodiment, the glycoarchaeol is a charged isoprenoid glycolipid comprising a sulfated saccharide group covalently linked to a free sn-1 hydroxyl group of a glycerol backbone of an archaeol core moiety via a beta linkage.

In an embodiment, the archaeol core moiety is 2,3-bis(((3,7,11)-3,7,11,15-tetramethylhexadecyl)oxy) propan-1-ol.

In an embodiment, the sulfated saccharide group is a sulfated disaccharide or trisaccharide. In an embodiment, the sulfated saccharide group is 6'-sulfate-β-D-Galp-(1,4)-β-D-Glcp.

In an embodiment, the glycoarchaeol is 2,3 bis[(3,7,11)-3,7,11,15-tetramethylhexadecyloxy]propan-1-yl 4-O-(6-β-sulfo-(3-D-galactopyranosyl)-β-D-glucopyranoside.

In an embodiment, the glycoarchaeol is of Formula I:

I

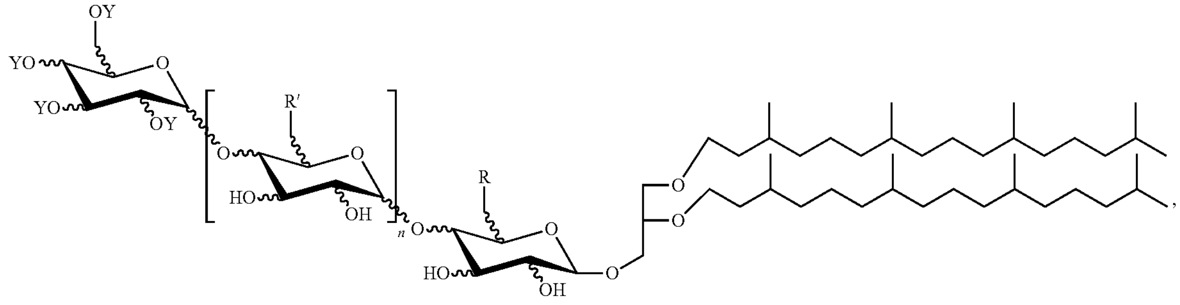

wherein n is 0 or 1;

R and R' are independently hydrogen or hydroxyl; and

Y is hydrogen or a sulfate group, and at least one Y is a sulfate group.

In an embodiment, the glycoarchaeol is of the structure:

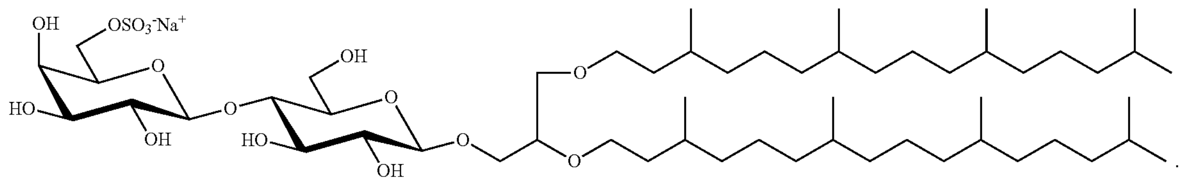

In an embodiment of an adjuvant composition as described herein, the pharmaceutically acceptable salt of the glycoarchaeol is a sodium, calcium or magnesium salt.

In an embodiment of an adjuvant composition as described herein, the glycoarchaeol or the pharmaceutically acceptable salt thereof is comprised within an archaeosome. In an embodiment, the archaeosome further comprises at least one additional lipid. In an embodiment, the at least one additional lipid is a neutrally charged or uncharged glycolipid. In a further embodiment, the at least one additional lipid is a lactosylarchaeol, a rhamnosyl-lactosylarchaeol, a triglucosylarchaeol, or a combination of any two or more thereof. In embodiments, the mol % ratio of the glycoarchaeol or the pharmaceutically acceptable salt thereof to the at least one additional lipid is from 99.9999:0.0001 to 30:70. In an embodiment, the mol % ratio of the glycoarchaeol or the pharmaceutically acceptable salt thereof to the at least one additional lipid is about 50:50.

In an embodiment of an adjuvant composition as described herein, the at least one immunostimulant or the pharmaceutically acceptable salt thereof comprises a TLR4 agonist, a TLR3 agonist, a TLR9 agonist, or a combination of any two or more thereof. In an embodiment, the TLR3 agonist is polyinosinic:polycytidylic acid Poly(I:C). In an embodiment, the TLR4 agonist is monophosphoryl lipid A (HFLA). In an embodiment, the TLR9 agonist is an oligonucleotide. In a further embodiment, the oligonucleotide comprises one or more CpG motifs.

In an embodiment of an adjuvant composition as described herein, the at least one immunostimulant comprises the saponin or the pharmaceutically acceptable salt thereof. In an embodiment, the saponin or the pharmaceutically acceptable salt thereof comprises a triterpene glycoside.

In an embodiment of an adjuvant composition as described herein, the at least one immunostimulant comprises QS-21.

In an embodiment of an adjuvant composition as described herein, the mass ratio of the glycoarchaeol or the pharmaceutically acceptable salt thereof to the at least one immunostimulant or the pharmaceutically acceptable salt thereof is from 100:1 to 100:50.

A further aspect is an immunogenic composition comprising an antigen and an adjuvant composition as described herein. In an embodiment, the antigen is a peptide, protein, or virus-like particle. In an embodiment, the immunogenic composition further comprises a pharmaceutically acceptable carrier. In an embodiment, the immunogenic composition is a vaccine composition. In an embodiment, the immunogenic composition is prepared by admixing the glycoarchaeol or the pharmaceutically acceptable salt thereof, the at least one immunostimulant, and the antigen. In an embodiment, the immunogenic composition is for parenteral or mucosal administration. In a further embodiment, the immunogenic composition is for intramuscular administration.

In an embodiment, the immunogenic composition elicits a cell-mediated response and a humoral response when administered to a subject. In an embodiment, the humoral response comprises an IgG response. In an embodiment, the cell-mediated response comprises at least one of a CD4+ response, a CD8+ response, a cytotoxic response, and production of at least one cytokine. In a further embodiment, the at least one cytokine comprises IFN-γ.

Another aspect is an immunogenic composition as described herein for use to induce an immune response in a subject. In an embodiment, the immune response comprises a cell-mediated response and a humoral response. In an embodiment, the humoral response comprises an IgG response. In an embodiment, the cell-mediated response comprises at least one of a CD4+ response, a CD8+ response, a cytotoxic response, and production of at least one cytokine. In a further embodiment, the at least one cytokine comprises IFN-γ.

Another aspect is a method of inducing an immune response in a subject, the method comprising administering to the subject an immunogenic composition as described herein. In an embodiment, the immune response comprises a cell-mediated response and a humoral response. In an embodiment, the humoral response comprises an IgG response. In an embodiment, the cell-mediated response comprises at least one of a CD4+ response, a CD8+ response, a cytotoxic response, and production of at least one cytokine. In a further embodiment, the at least one cytokine comprises IFN-γ. In an embodiment, the immunogenic composition is administered to the subject by parenteral or mucosal administration. In a further embodiment, the immunogenic composition is administered to the subject by intramuscular administration.

Another aspect is a method of preparing an immunogenic composition, the method comprising combining an antigen with an adjuvant composition as described herein.

DETAILED DESCRIPTION

Definitions

Figure 1:
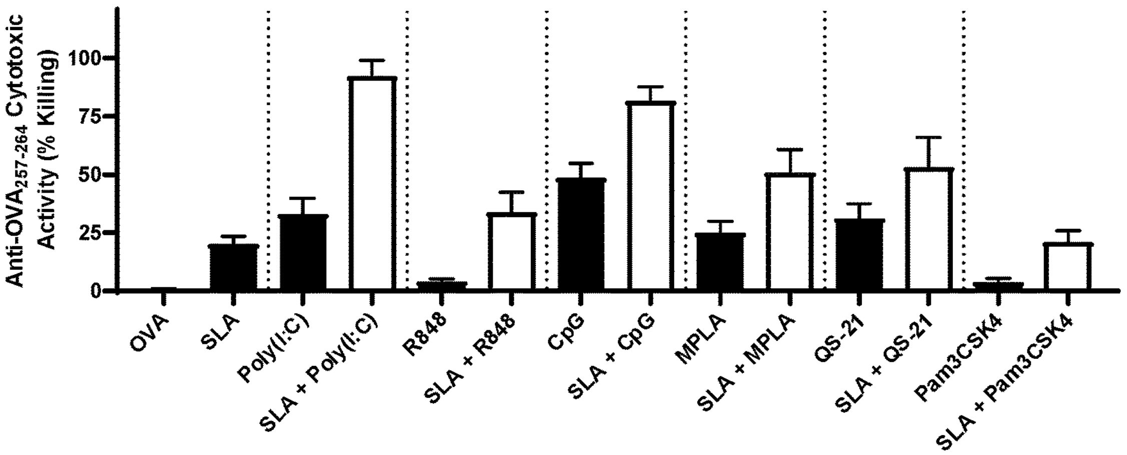
FIG. 1 shows in vivo CTL activity of different adjuvants and adjuvant combinations. Target cells were formed by pulsing CFSE-labeled splenocytes from naïve mice with a CD8 epitope peptide from ovalbumin (OVA) which were then transferred to immunized mice. On the following day (Day 28: 7 days post $2^{nd}$ immunization by intramuscular route), splenocytes were collected and the levels of the target cells determined by flow cytometry. Grouped data is presented as mean+SEM (n=10/group).

As used herein, the following terms may have the meanings ascribed to them below, unless specified otherwise. However, it should be understood that other meanings that are known or understood by those having ordinary skill in the art are also possible, and within the scope of the present disclosure. In the case of conflict, the present disclosure, including definitions, will control. In addition, the materials, methods, and examples provided herein are illustrative only and not intended to be limiting.

Where a range of values is provided, it is to be understood that each intervening value, to the tenth of the unit of the lower limit unless the context clearly dictates otherwise, between the upper and lower limit of that range and any other stated or intervening value in that stated range is encompassed within the description. Ranges from any lower limit to any upper limit are contemplated.

The term "about" as used herein may be used to take into account experimental error, measurement error, and variations that would be expected by a person having ordinary skill in the art. For example, "about" may mean plus or minus 10%, or plus or minus 5%, of the indicated value to which reference is being made.

As used herein the singular forms "a", "an", and "the" include plural references unless the context clearly dictates otherwise.

The phrase "and/or", as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of".

As used herein, all transitional phrases such as "comprising," "including," "carrying," "having," "containing," "involving," "holding," "composed of", and the like are to be understood to be open-ended, i.e., to mean including but not limited to. Only the transitional phrases "consisting of" and "consisting essentially of" shall be closed or semi-closed transitional phrases, respectively.

As used herein, the phrase "at least one" or "one or more", in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

As used herein, the term "adjuvant" refers to an agent that increases and/or directs specific immune responses to an antigen.

As used herein, the term "immunostimulant" refers to an agent that stimulates an immune response when introduced into a subject.

As used herein, the term "glycoarchaeol" refers to a glycolipid comprising a saccharide moiety and a core lipid moiety selected from an archaeol core moiety and a caldarchaeol core moiety. The saccharide moiety may be a monosaccharide moiety or an oligosaccharide moiety, such as a disaccharide, trisaccharide, or other polysaccharide. Stereochemistry at the chiral centers of sugar molecules may be R or S configurations, or any combination thereof. An archaeol core moiety is a diether lipid structure commonly found in archaea comprising two phytanyl chains linking to the sn-2 and sn-3 positions of a glycerol molecule (sn-2,3-diphytanylglycerol diether). Stereochemistry at the chiral centers of the archaeol core moiety may be R or S configurations, or any combination thereof. A caldarchaeol core moiety, which is a dimer of an archaeol core moiety, is a tetraether lipid structure commonly found in archaea comprising glycerol molecules that are connected by two phytanyl chains (sn-2,3-dibiphytanylglycerol tetraether). As used herein, the terms "archaeol core moiety" and "caldarchaeol core moiety" include lipid structures of natural, semi-synthetic, and synthetic origin. In a glycoarchaeol, the core lipid moiety is bound to the saccharide moiety by ether linkage at the sn-1 position of a glycerol.

The term "Toll-like receptor (TLR) agonist" refers to an agonist that targets one or more Toll-like receptors (TLRs). TLRs are a family of transmembrane pattern recognition receptors that sense pathogens or endogenous damage signals and initiate the innate and adaptive immune response. There are ten functional TLRs known in humans (TLR 1-10), but additional TLRs are known in other organisms. For example, mice have twelve TLRs (TLR1-9 and 11-13).

Saponins are a group of molecules comprising a triterpene or steroid aglycone with one or more sugar chains. Saponins are primarily found in plants, but they can be produced by other organisms, such as starfish and sea cucumbers. As used herein, the term "saponin" includes naturally derived saponins, synthetic saponins, and saponin derivatives; including semi-synthetic saponin derivatives, such as those described in Moses et al (2014).

As used herein, the term "pharmaceutically acceptable salt" refers to a derivative of the disclosed compound, wherein the parent compound is modified by making an acid or base salt thereof. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from nontoxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

As used herein, the term "pharmaceutically acceptable carrier" refers to a vehicle that is compatible with pharmaceutical administration. Pharmaceutically acceptable carriers known in the art include, but are not limited to, sterile water, saline, glucose, and buffered solutions. Pharmaceutically acceptable carriers may include auxiliary agents including, but not limited to, diluents, stabilizers (e.g. sugars and amino acids), preservatives, wetting agents, emulsifying agents, pH buffering agents, viscosity enhancing additives, colorants and the like.

As used herein, the term "vaccine composition" refers to a composition, comprising at least one antigen or immunogen, or comprising a nucleic acid molecule encoding at least one antigen or immunogen, in a pharmaceutically acceptable carrier, that is useful for inducing an immune response against the antigen or immunogen in a subject, for the purpose of improving immunity against a disease and/or infection in the subject. Common examples of antigens and immunogens include proteins, peptides, and polysaccharides. Some antigens include lipids and/or nucleic acids in combination with proteins, peptides and/or polysaccharides.

As used herein, the term "peptide" refers to a polypeptide comprising two or more amino acids covalently linked by peptide bonds. The term "peptide" is typically used to refer to a short polypeptide comprising between two and fifty amino acids, though "peptide" may also be used to refer to longer polypeptides. Similarly, a "polypeptide" may be of any length, provided it includes at least two amino acids.

As used herein, the term "protein" refers to a biomolecule comprising one or more polypeptides. Typically, the term "protein" is used to describe a polypeptide that is greater than 50 amino acids in length, though this term may also be used to describe polypeptides comprising 50 or fewer amino acids. A protein may have primary, secondary, tertiary, and/or quaternary structure. Additionally, a protein may comprise functional groups such as lipids, carbohydrates, phosphate groups, methyl groups, S-nitrosyl groups, and N-acetyl groups.

As used herein, the term "virus-like particle" (VLP) refers to a non-infectious particle formed by self-assembly of structural (e.g. envelope and/or capsid) proteins from a virus, without incorporating genetic material of the virus.

As used herein, "parenteral administration" refers to non-oral administration, typically by injection or infusion. Examples of parenteral administration include subcutaneous administration, intraperitoneal administration, intravenous administration, intradermal administration, and intramuscular administration.

As used herein, "mucosal administration" refers to administration to a mucosa to allow for transmucosal delivery. Examples of mucosal administration include nasal administration, rectal administration, vaginal administration, ocular administration, sublingual administration, buccal administration, and oral cavity administration.

As used herein, the term "cell-mediated response" refers to an immune response characterized by an expanded population of specific T-cells that, in the presence of a recognized antigen, produce cytokines locally. A "cell-mediated response" may interchangeably be referred to as "cell-mediated immunity" (CMI) or a "cell-mediated immune response". Cell-mediated immunity usually comprises CD4 T cells producing cytokines. A cell-mediated response may comprise at least one of a CD4+ response, a CD8+ response, and a cytotoxic response. As used herein, the terms "CD8+ response" and "cytotoxic response" are distinct from Th1/Th2 immune responses, with CD8 T cells representing a specific subset of T cells whose main role is to directly kill infected and cancerous cells. In contrast, Th1/Th2 balance is indicative of the inflammatory character of CD4 T cells specifically. For example, the production of IFN-g by CD4 cells is indicative of a Th1 response. While a subset of CD4 T cells can have cytotoxic activity, most CD4 T cells function as helper cells that do not directly kill cells identified as foreign but rather help determine how the immune system responds.

As used herein, the term "humoral response" refers to an immune response that is mediated by macromolecules found in extracellular fluids, such as secreted antibodies, complement proteins, and certain antimicrobial peptides. Antibodies, which may be interchangeably referred to as immunoglobulins, are antigen-binding proteins that are secreted by activated B-cells. A "humoral response" may interchangeably be referred to as "humoral immunity", a "humoral immune response", or "antibody-mediated immunity".

As used herein, the term "subject" refers to an animal, including both human and non-human animals. Examples of non-human subjects include, but are not limited to, pets, livestock, and animals used for antibody production and/or vaccine research and development. Examples of animals used for antibody production and/or vaccine research and development include, but are not limited to, rodents, rabbits, ferrets, non-human primates, swine, sheep, and cattle.

Description

Provided is an adjuvant composition comprising: a glycoarchaeol or a pharmaceutically acceptable salt thereof, and at least one immunostimulant selected from a Toll-like receptor (TLR) agonist or a pharmaceutically acceptable salt thereof and a saponin or a pharmaceutically acceptable salt thereof. The core lipid moiety in the glycoarchaeol may be obtained by chemical synthesis, or from the polar lipids of an archaebacterium, such as, but not limited to, *Halobacterium salinarum*. In an embodiment, the glycoarchaeol comprises an archaeol core moiety. In embodiments, the glycoarchaeol may be a synthetic glycoarchaeol or a semi-synthetic derivative of a naturally occurring glycoarchaeol. Methods to produce synthetic archaeols are known in the art, as demonstrated, for example, by Aoki and Poulter (1985). In some embodiments, the glycoarchaeol may be a sulfated glycoarchaeol as described in U.S. Pat. No. 10,647,737.

In some embodiments, the glycoarchaeol is negatively charged and comprises one or more sulfate moieties added to the saccharide group of the glycoarchaeol. Archaeol stable to harsh synthesis conditions as it typically has stable ether linkages to saturated isoprenoid chains. The result is a sulfated-glycolipid that readily hydrates to form stable structures capable of entrapping a compound, such as, but not limited to, proteins and peptides, for enhancing immune responses to co-administered antigen(s). However, entrapment of the compound may not be required for the immune response to be enhanced. Admixing the sulfated-glycolipid with an antigen can result in an enhanced immune response to the antigen. The sulfated saccharide group will comprise at least one sulfate moiety. In certain non-limiting embodiments, the at least one sulfate moiety may be positioned at the 6' position of the terminal monosaccharide moiety. In an embodiment, the sulfated saccharide group comprises only one sulfate moiety.

The sulfated saccharide group may comprise one or more monosaccharide moieties including a mannose (Man) moiety, a glucose (Glc) moiety, a rhamnose (Rha) moiety, or a galactose (Gal) moiety, or any combination of two or more thereof. In further embodiments, the sulfated saccharide group may be a sulfated oligosaccharide group, such as a sulfated disaccharide or trisaccharide group. In an embodiment, the sulfated oligosaccharide group may be a sulfated lactosyl group, or more specifically, a 6'-S-lactosyl group. In other embodiments, the sulfated lactosyl group is 6'-sulfate-β-D-Galp-(1,4)-β-D-Glcp.

The core lipid moiety may be an archaeol core moiety or a caldarchaeol core moiety. In an embodiment, the archaeol moiety is 2,3-bis(((3,7,11)-3,7,11,15-tetramethylhexadecyl) oxy) propan-1-ol.

In another embodiment, the glycoarchaeol is a charged isoprenoid glycolipid comprising a sulfated saccharide group covalently linked to the free sn-1 hydroxyl group of the glycerol backbone of the archaeol core moiety via a beta linkage. In an embodiment, the glycoarchaeol is 2,3bis[(3,7,11)-3,7,11,15-tetramethylhexadecyloxy]propan-1-yl 4-O-(6-O-sulfo-β-D-galactopyranosyl)-β-D-glucopyranoside.

In a further embodiment, the immunogenic composition comprises at least one immunostimulant selected from a Toll-like receptor (TLR) agonist or a pharmaceutically acceptable salt thereof and a saponin or a pharmaceutically acceptable salt thereof, and a glycoarchaeol of the following formula (Formula I) or a pharmaceutically acceptable salt thereof.

I

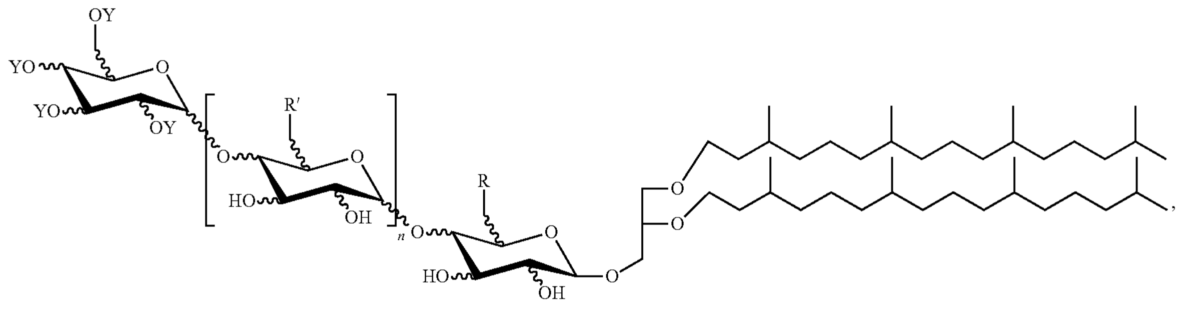

wherein n is 0 or 1; R and R' are independently hydrogen or hydroxyl; and Y is hydrogen or a sulfate group, and at least one Y is a sulfate group. Curly bonds indicate either R or S stereochemistry at the sugar atoms, and include all possible combinations of stereochemistry.

In an embodiment of the glycoarchaeol defined by the compound of Formula I, n is 0 and R is OH. In this embodiment, the sulfated saccharide group may comprise mannose (Man) moieties, glucose (Glc) moieties, or galactose (Gal) moieties; or any combination of two different moieties selected from a mannose moiety, a glucose moiety, and a galactose moiety.

In yet further embodiments, the glycoarchaeol may be one of the following compounds: 6'-sulfate-α-D-Manp-(1,6)-β-D-Galp-(1,4)-β-D-Glcp-(1,1)-archaeol, 6'-sulfate-β-D-Glcp-(1,6)-β-D-Galp-(1,4)-β-D-Glcp-(1,1)-archaeol, or 6'-sulfate-β-D-Galp-(1,4)-β-D-Glcp-(1,6)-β-D-Glcp-(1,1)-archaeol.

In an embodiment, the glycoarchaeol is sodium (2R)-2,3-Bis[(3R,7R,11R)-3,7,11,15-tetramethylhexadecyloxy]propan-1-yl-4-O-(6-O-sulfo-β-D-galactopyranosyl)-β-D-glucopyranoside, and has the structure:

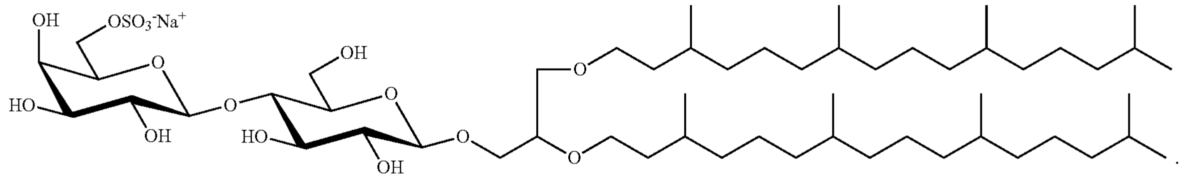

A glycoarchaeol as described herein may be present as a pharmaceutically acceptable salt. The pharmaceutically acceptable salt may be any salt that is compatible with pharmaceutical administration. Many pharmaceutically compatible salts will be known to one skilled in the art and they include, for example, potassium, calcium, aluminum, sodium, zinc, and lithium salts. In an embodiment, the pharmaceutically acceptable salt is a sodium, calcium or magnesium salt; though any salt known to be pharmaceutically compatible and active may be employed.

In some embodiments, the mass ratio of the glycoarchaeol to the at least one immunostimulant is from 100:1 to 100:50. For example, the mass ratio may be from 100:1 to 100:50, from 100:10 to 100:50, from 100:30 to 100:50, from 100:40 to 100:50, from 100:1 to 100:40, from 100:1 to 100:30, from 100:1 to 100:20, or from 100:20 to 100:40; or any range or subrange within the preceding ranges.

In some embodiments, the glycoarchaeol is comprised within an archaeosome. An archaeosome is a liposome (lipid vesicle) comprising one or more ether lipids that are unique to the domain of archaeabacteria. Archaeosomes may be made from natural archaeal membrane glycolipids and/or synthetic or semi-synthetic glycolipids or glycolipid analogues. Archaeal-type glycolipids typically consist of archaeol (diether) and/or caldarchaeol (tetraether) core structures in which regularly branched and usually fully saturated phytanyl chains (20-40 carbons in lengths), are attached via ether bonds to the sn-2,3 carbons of a glycerol backbone (Benvegnu et al, 2009).

In some embodiments, the archaeosome further comprises at least one additional lipid. In an embodiment, the at least one additional lipid is a neutral or uncharged glycolipid. In an embodiment, the at least one additional lipid is lactosylarchaeol, rhamnosyl-lactosylarchaeol, triglucosylarchaeol, or a combination of any two or more thereof. In an embodiment, the mol % ratio of the glycoarchaeol to the at least one additional lipid is from 99.9999:0.0001 to 30:70. For example, the mol % ratio of the glycoarchaeol to the at least one additional lipid may be from 99.9999:0.0001 to 30:70, from 90:10 to 30:70, from 80:20 to 30:70, from 70:30 to 30:70, from 60:40 to 30:70, from 50:50 to 30:70, from 40:60 to 30:70, from 35:65 to 30:70, from 55:45 to 45:55, or from 60:40 to 40:60. The mol % ratio may also be any range or subrange within these ranges. In an embodiment, the mol % ratio of the glycoarchaeol to the at least one additional lipid is about 50:50.

In further embodiments, the archaeosome may be formulated to have a surface charge ranging from about −20 mV to about −70 mV. As an example, the archaeosome may comprise 6'-sulfate-lactosylarchaeol and uncharged lactosylarchaeol in a mol % ratio of from 100:0 to 30:70, or about 50:50, in which case the surface charge of the archaeosome may preferably be from about −25 to about −45 mV.

The archaeosomes may, in particular embodiments, have an average diameter of between about 50 nm and about 350 nm.

In an embodiment, the at least one immunostimulant comprises a TLR3 agonist, a TLR4 agonist, a TLR9 agonist, or a combination of any two or more thereof. Examples of TLR3 agonists include virally-derived double- or singlestranded RNA and synthetic RNA oligoribonucleotides (ORNs) such as polyinosinic-polycytidylic acid (Poly(I:C)). Examples of TLR4 agonists include lipopolysaccharide (LPS) and its derivative monophosphoryl lipid A (MPLA) as well as synthetic agonists such as Glucopyranosyl Lipid Adjuvant (GLA). Examples of TLR9 agonists include microbial and viral oligonucleotides and synthetic oligonucleotides comprising unmethylated CpG motifs (CpG ODNs). The TLR3 agonist may be Poly(I:C) or a Poly(I:C) derivative such as poly-IC12U (Ampligen®) or poly-ICLC (Hiltonol®), for example as described in Martins et al (2014); the TLR4 agonist may be monophosphoryl lipid A (MPLA); and the TLR9 agonist may be an oligonucleotide, which may comprise one or more CpG motifs.

In an embodiment, the at least one immunostimulant comprises a saponin. A wide variety of saponins are known in the art, for example as described in Moses et al (2014) and Hickie et al (2011). In an embodiment, the saponin is a triterpene glycoside, also known as a triterpenoid saponin. In an embodiment, the at least one immunostimulant comprises QS-21 or an active component of QS-21. QS-21 is a fraction of an extract from the soap bark tree (*Quillaja saponaria*) that comprises a mixture of soluble triterpene glycosides (Rajupathi et al, 2011).

Further provided is an immunogenic composition comprising an adjuvant composition as described herein together with an antigen. Non-limiting examples of antigens include toxoids; chemicals; infectious agents such as bacteria, viruses, or fungi (which may be attenuated or killed); proteins; peptides; polysaccharides, and conjugate molecules. The immunogenic composition may be a vaccine composition.

The immunogenic composition may further comprise a pharmaceutically acceptable carrier. Non-limiting examples of pharmaceutically acceptable carriers include water, saline, glucose, and buffered solutions. Pharmaceutically acceptable carriers may also include additional agents, for example, auxiliary agents such as diluents, stabilizers, preservatives, wetting agents, emulsifying agents, pH buffering agents, viscosity enhancing additives, and colorants.

In an embodiment, the immunogenic composition is prepared by admixing the at least one immunostimulant and the antigen.

An immunogenic composition as described herein may be administered by any suitable means as would be understood to one skilled in the art. Non-limiting examples of common delivery methods for immunogenic compositions include oral administration, subcutaneous administration, intramuscular administration, intradermal administration, and intranasal administration. In an embodiment, the immunogenic composition is delivered by parenteral or mucosal administration. In a further embodiment, the immunogenic composition is delivered by intramuscular administration.

An immunogenic composition as described herein may elicit both a cell-mediated response and a humoral response when administered to a subject. Various cell-mediated and humoral responses are possible, as will be understood to one skilled in the art. For example, mammals have five antibody types (IgA, IgD, IgE, IgG, and IgM) and different types of antibodies may be produced in response to different antigens. Similarly, a cell-mediated immune response may include a type 1 response, a type 2 response, and/or a type 3 response; each of which involves different cell types and cytokines (Annunziato et al, 2015). In an embodiment, the humoral response comprises an IgG response. In an embodiment, the cell-mediated response comprises at least one of a CD4+ response, a CD8+ response, a cytotoxic response, and production of at least one cytokine. In an embodiment, the cytokine comprises IFN-γ.

An immunogenic composition as described herein may be for use to induce an immune response in a subject. Further provided is use of an immunogenic composition as described herein to induce an immune response in a subject. Also provided is a method of inducing an immune response in a subject, the method comprising administering to the subject an immunogenic composition as described herein. The immune response resulting from the use or method may be as described herein.

Also provided is a method of preparing an immunogenic composition, the method comprising combining an adjuvant composition as described herein with an antigen.

EXAMPLES

The following non-limiting examples are illustrative of aspects of the present disclosure:

Example 1: Preparation of Adjuvant-Antigen Combinations

Sulfated lactosyl archaeol (SLA; 6'-sulfate-β-D-Galp-(1,4)-β-D-Glcp-(1,1)-archaeol) was synthesized as described previously (Whitfield et al, 2010) and archaeosomes were prepared as described previously (Jia et al, 2019). Briefly, 30 mg of SLA lipid was dissolved in chloroform/methanol; a thin film was formed after removal of solvent under $N_2$ gas with mild heating. A vacuum was applied to ensure total removal of trace solvents. For preparation of pre-formed SLA archaeosomes, dried lipids were first hydrated in 700 μL of Milli-Q water without protein antigen. Lipid dispersions were shaken for 2-3 hours at 40° C. to 50° C. until completely suspended. Next, a brief sonication was applied at 40° C. in an ultrasonic water bath (Fisher Scientific, Ottawa, ON, Canada) for up to 60 minutes until the desired particle size (between 100 nm and 200 nm) was obtained. Approximately, 300 μL of 10×PBS (Millipore Sigma Canada, Oakville, Ontario) was added to balance osmolality and reach pH=7.4. The pre-formed empty SLA archaeosomes were stored at 4° C. with a concentration of 30-40 mg/mL until used.

All toll-like receptor agonists (i.e., CpG, MPLA, $Pam_3CSK_4$, Poly(I:C), and Resiquimod (R848)) were purchased from InvivoGen (Headquarter CA, USA). QS-21 was purchased from Desert King (San Diego, CA, USA). Stock solutions were prepared according to manufacturer's instructions, at 1 mg/mL for CpG, MPLA, $Pam_3CSK_4$, R848 and QS-21 and 3-10 mg/mL for Poly(I:C).

Antigen stock solutions for ovalbumin protein (OVA; type VI, Sigma-Aldrich, St. Louis, MO, USA) and recombinant HBsAg (HBsAg; Subtype adw; Fitzgerald Industries International, Acton, MA, USA) were prepared at a concentration of 1 mg/mL. The OVA (amino acids 253-277: LEQLESIINFEKLTEWTSSNVMEER, SEQ ID NO: 1), Tryp1 (amino acids 447-470: VTNIEMFVTAPDNLGYMYEVQWPG, SEQ ID NO: 2), PMEL (amino acids 17-41: ALLAVGALEGPRNQDWLGVPRQLVT, SEQ ID NO: 3) and Trp2 (amino acids 172-196: TQPQIANCSVYDFFVWLHYYSVRDT, SEQ ID NO: 4) long peptides were synthesized by JPT Peptide Technologies GmbH, Berlin, Germany. Based on their solubility profiles, the OVA, Tryp1, PMEL and Trp2 peptides were dissolved at 4.4 mg/mL in PBS/0.1 M NaOH, 10 mg/mL in PBS, 8 mg/mL in water and 40 mg/mL in DMSO, respectively.

Vaccine compositions comprising a single adjuvant (SLA, CpG, Poly(I:C), MPLA, R848, $Pam_3CSK_4$ or QS-21) were prepared as previously described for SLA (Jia et al, 2019) or as per manufacturer's instructions for other adjuvants.

Using ovalbumin (OVA) as antigen, the combination adjuvant formulations were prepared by first mixing empty pre-formed SLA archaeosomes with an additional adjuvant (Poly(I:C), CpG, MPLA, R848, $Pam_3CSK_4$ or QS-21) and briefly vortexing. Thereafter, OVA antigen solution was added and briefly vortexed. PBS buffer was added to give required concentration for immunization. The final dose concentration of each component is indicated in Table 1.

Using HBsAg as antigen, the combination adjuvant formulations were prepared by first mixing empty pre-formed SLA archaeosomes with either Poly(I:C) or CpG and briefly vortexing. Thereafter, HBsAg antigen solution was added and briefly vortexed. PBS buffer was added to the admixture to give required formulation for immunization. The final dose concentration of each component is indicated in Table 2.

Using long peptides (LP) as antigen, the combination adjuvant formulations were prepared by first mixing required volume of PBS vehicle and adjuvants (empty pre-formed SLA archaeosomes and/or Poly(I:C)) and briefly vortexing. Thereafter, OVA long-peptide or a combination of Tryp1, PMEL and Trp2 long-peptides were added and briefly vortexed. The final dose concentration of each components is indicated in Table 3.

TABLE 1

Vaccine compositions using OVA protein as antigen

| Grp No. (N = 10) | Adjuvant | Adjuvant dose µg/50 µL | Antigen dose µg/50 µL |
|---|---|---|---|
| 1 | None (OVA alone) | — | 5 |
| 2 | SLA Admixed | 500 | 5 |
| 3 | Resiquimod (R848) | 5 | 5 |
| 4 | CpG | 5 | 5 |
| 5 | MPLA | 5 | 5 |
| 6 | QS-21 | 5 | 5 |
| 7 | $Pam_3CSK_4$ | 5 | 5 |
| 8 | Poly(I:C) | 20 | 5 |
| 9 | SLA + R848 | 500 + 5 | 5 |
| 10 | SLA + CpG | 500 + 5 | 5 |
| 11 | SLA + MPLA | 500 + 5 | 5 |
| 12 | SLA + QS-21 | 500 + 5 | 5 |
| 13 | SLA + $Pam_3CSK_4$ | 500 + 5 | 5 |
| 14 | SLA + Poly(I:C) | 500 + 20 | 5 |

TABLE 2

Vaccine compositions using HBsAg (virus-like particle) as antigen

| Grp No. (N = 5) | Adjuvant | Adjuvant dose µg/50 µL | Antigen dose µg/50 µL |
|---|---|---|---|
| 1 | None (HBsAg alone) | — | 2 |
| 2 | SLA | 1000 | 2 |
| 3 | Poly(I:C) | 40 | 2 |
| 4 | SLA + Poly(I:C) | 1000 + 40 | 2 |
| 5 | CpG | 10 | 2 |
| 6 | SLA + CpG | 1000 + 10 | 2 |

TABLE 3

Vaccine compositions using long peptides (LP) as antigen

| Grp No. (N = 5) | Antigen | Adjuvant | Adjuvant dose µg/50 µL | Antigen dose µg/50 µL |
|---|---|---|---|---|
| 1 | OVA LP | none | none | 30 |
| 2 | OVA LP | SLA | 1000 | 30 |
| 3 | OVA LP | Poly(I:C) | 50 | 30 |
| 4 | OVA LP | SLA + Poly(I:C) | 1000 + 50 | 30 |
| 5 | Tryp1, PMEL, Trp2 LP | none | none | 30 (each peptide) |
| 6 | Tryp1, PMEL, Trp2 LP | SLA | 1000 | 30 (each peptide) |
| 7 | Tryp1, PMEL, Trp2 LP | Poly(I:C) | 50 | 30 (each peptide) |
| 8 | Tryp1, PMEL, Trp2 LP | SLA + Poly(I:C) | 1000 + 50 | 30 (each peptide) |

Example 2: Testing in Vivo CTL Activity

Figure 6:
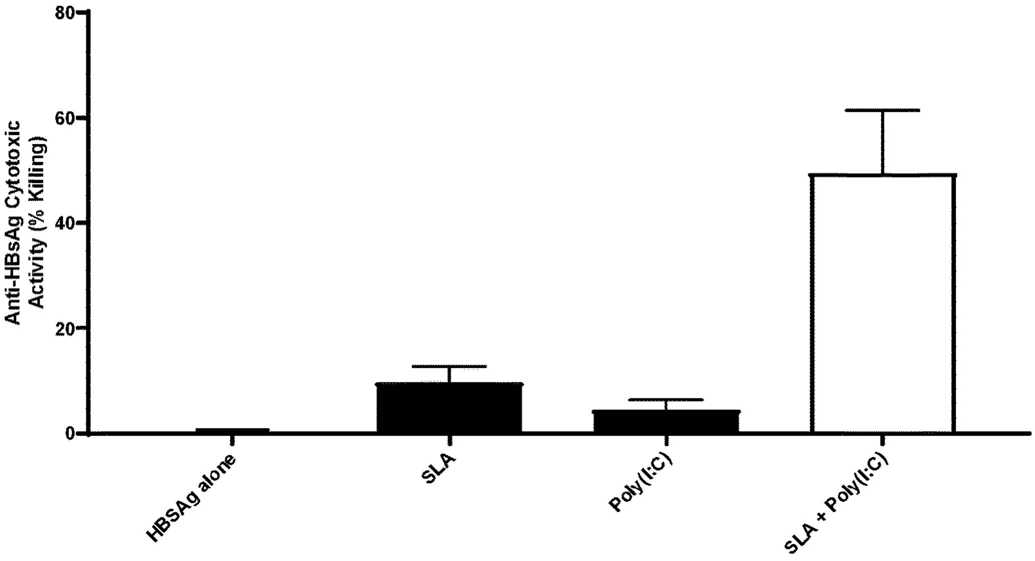
FIG. 6 shows in vivo CTL activity. Mice were immunized on days 0 & 21 with hepatitis B surface antigen, HBsAg, alone or formulated with SLA archaeosomes, Poly(I:C) or a combination of SLA+Poly(I:C). Target cells were prepared by pulsing CFSE-labeled splenocytes from naïve mice with CD8 epitope peptide from HbsAg. These were transferred to immunized mice on Day 27, and the following day (Day 28: 7 days post $2^{nd}$ immunization), splenocytes were collected and the % killing of target cells determined by flow cytometry. Grouped data is presented as mean+SEM (n=5/group).

Mice were immunized with OVA or HBsAg formulations on days 0 and 21, with spleens collected on Day 28, 7 days following second vaccination, for measurement of in vivo cytolytic activity. In vivo cytolytic activity in immunized mice was enumerated as described previously (Barber et al, 2003). Donor spleen-cell suspensions from syngeneic unimmunized mice were prepared. Cells were split into two aliquots. One aliquot was incubated with the appropriate CTL-specific peptide (10 µM; SIINFEKL, SEQ ID NO: 6 for OVA experiments and IPQSLDSWWTSL, SEQ ID NO: 5 for HBsAg experiments; JPT Peptide Technologies GmbH) in R10 media. After 30 minutes of incubation, the control non-pulsed aliquot was stained with low concentration of CFSE (0.25 µM; Thermo Fisher Scientific) and the second peptide-pulsed aliquot was stained with 10×CFSE (2.5 µM). The two cell aliquots were mixed 1:1 and injected ($20\times10^6$ cells per mouse) into previously immunized recipient mice. At ~20 to 22 h after the donor cell transfer, spleens were removed from recipients, single cell suspensions prepared, and cells analyzed by flow cytometry on a BD Fortessa™ flow cytometer (Becton Dickenson). The in vivo lysis percentage of peptide pulsed targets was enumerated according to the equation provided in Barber et al (2003). With OVA-immunized animals, the combination of SLA+Poly(I:C) or SLA+CpG resulted in >80% killing of SIINFEKL (SEQ ID NO: 6)-labeled cells, while the killing observed with each of the adjuvants on their own (i.e. SLA, Poly(I:C) or CpG) was <50% (FIG. 1). Some additive effects were also seen when SLA was combined with MPLA or QS-21, but the activity (~50%) was not as high as seen when SLA was combined with Poly(I:C) or CpG. In OVA-immunized animals, the use of SLA in combination with R848 or $Pam_3CSK_4$ as an adjuvant composition did not result in an increase in CTL activity as compared to SLA used alone as adjuvant. The synergy between SLA and Poly(I:C) with regards to cytolytic activity was further confirmed when animals were immunized with HBsAg-adjuvanted formulations and injected with cells labeled with the HBsAg CD8 epitope IPQSLDSWWTSL (SEQ ID NO: 5). 50% killing was observed in mice receiving HBsAg adjuvanted with SLA+Poly(I:C), while <10% killing was observed in mice immunized with formulations containing antigen with either SLA or Poly(I:C) alone (FIG. 6).

Example 3: Testing IFN-Gamma Secretion by ELISpot Assay

Figure 2:
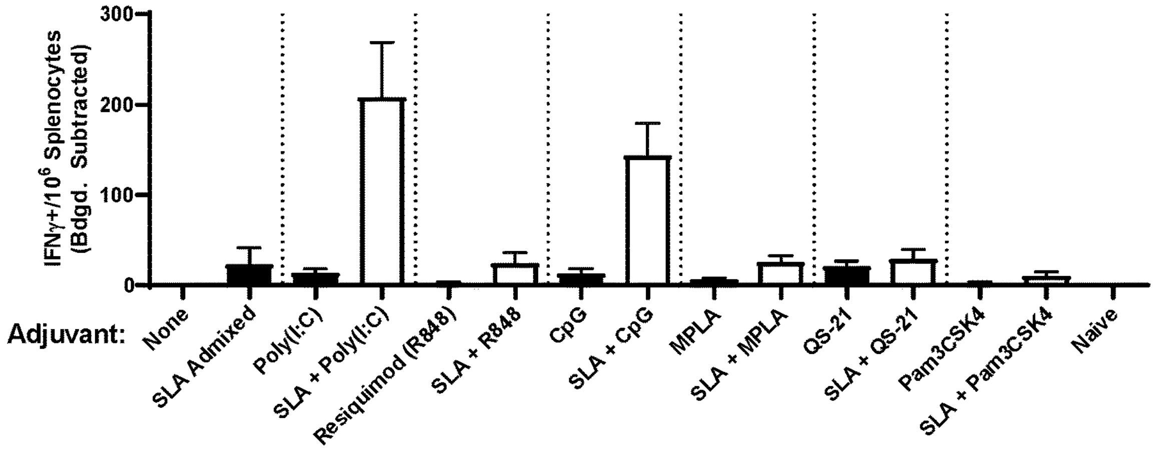
FIG. 2 shows OVA-specific cellular responses assayed by IFN-gamma secretion (CD8+ T cells). Splenocytes of mice immunized with OVA antigen alone (none) or formulated with SLA archaeosomes, other adjuvants (Poly(I:C), Resiquimod (R848), CpG, MPLA, QS-21, $Pam_3CSK_4$) or SLA in combination with other adjuvants were collected on Day 28 (7 days post $2^{nd}$ immunization) and analyzed by IFN-γ ELISpot when stimulated by CD8 epitope peptide. Grouped data is presented as mean+SEM (n=10/group).
Figure 3:
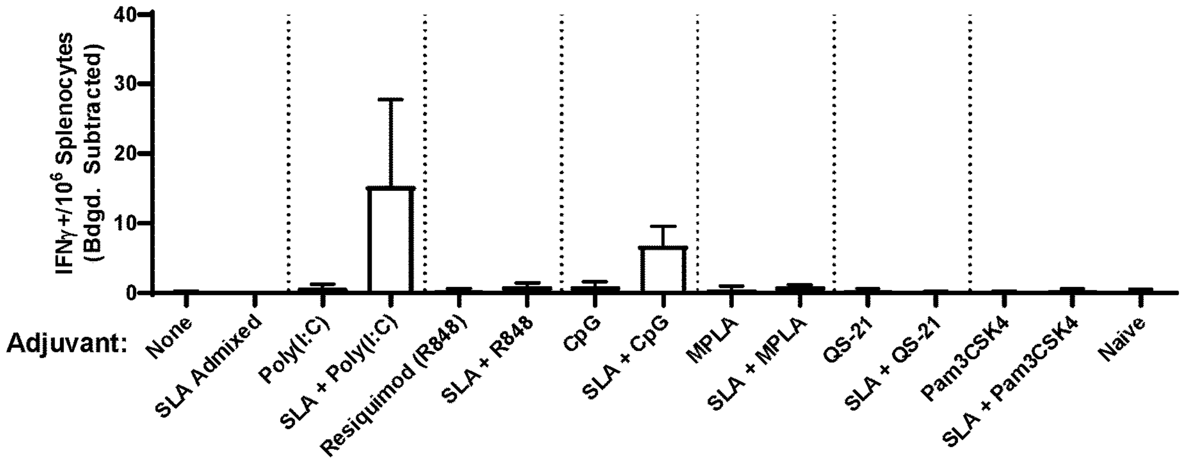
FIG. 3 shows ovalbumin (OVA)-specific cellular responses assayed by IFN-gamma secretion (CD4+ T cells). Splenocytes of mice immunized with OVA antigen alone (none) or formulated with SLA archaeosomes, other adjuvants (Poly(I:C), Resiquimod (R848), CpG, MPLA, QS-21, $Pam_3CSK_4$) or SLA in combination with other adjuvants were collected on Day 28 (7 days post $2^{nd}$ immunization) and analyzed by IFN-γ ELISpot when stimulated by OVA CD4 epitope peptide. Grouped data is presented as mean+SEM (n=10/group).
Figure 9:
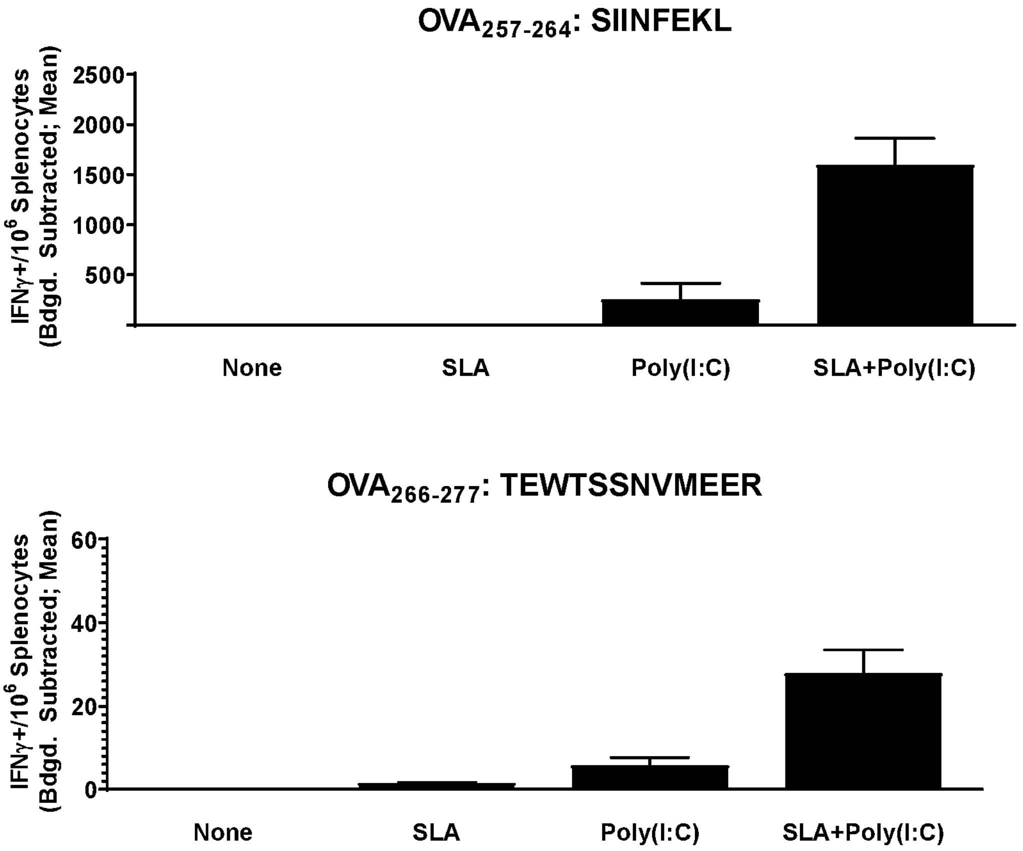
FIG. 9 shows OVA-specific cellular responses analyzed by IFN-γ ELISpot. Splenocytes of mice immunized with OVA long peptide alone or formulated with SLA archaeosomes, Poly(I:C) or a combination of SLA+Poly(I:C) were collected on Day 28 (7 days post $3^{rd}$ immunization) and analyzed by IFN-γ ELISpot when stimulated with OVA CD8 (top) or CD4 (bottom) epitope peptides. Grouped data is presented as mean+SEM (n=5/group).
Figure 10:
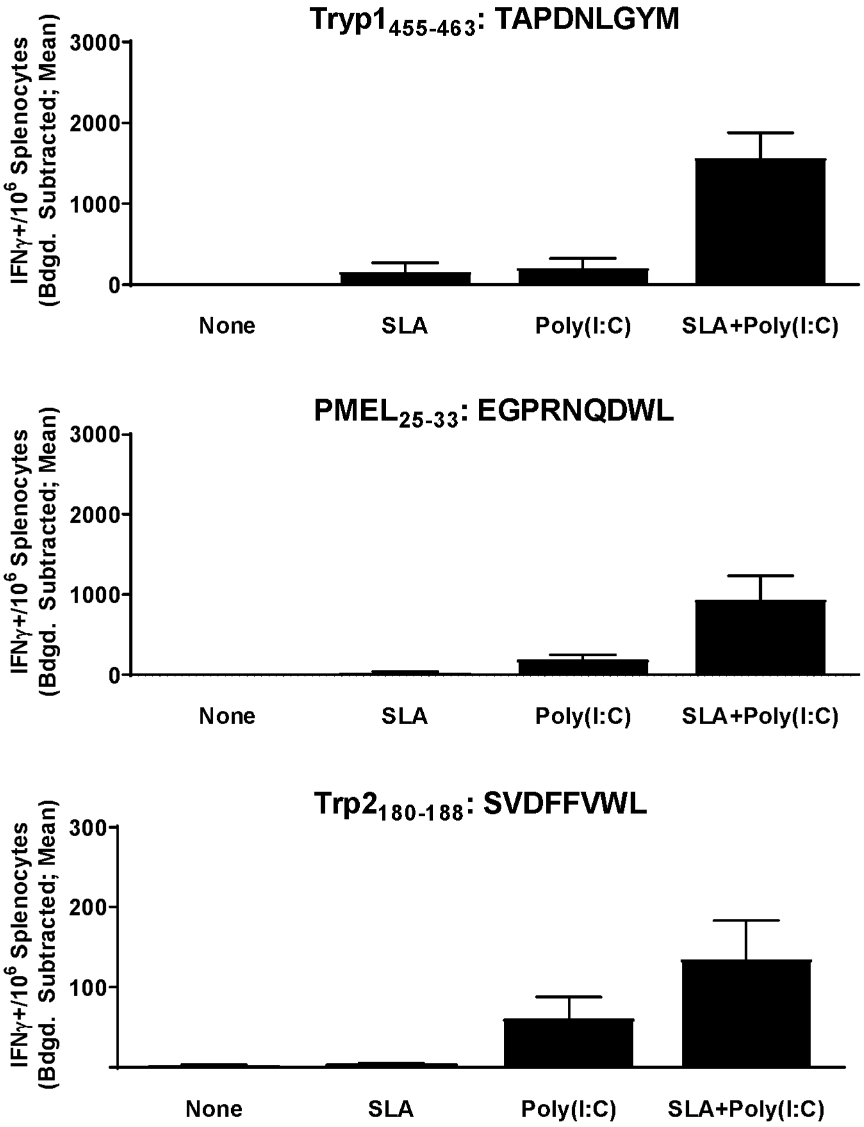
FIG. 10 shows tumor associated antigen-specific cellular responses analyzed by IFN-γ ELISpot. Splenocytes of mice immunized with 3 long peptides covering CD8 epitopes form Tryp1, PMEL and Trp2 alone or formulated with SLA archaeosomes, Poly(I:C) or SLA+Poly(I:C) were collected on Day 28 (7 days post $3^{rd}$ immunization) and analyzed by IFN-γ ELISpot when stimulated with the CD8 epitope peptides. Grouped data is presented as mean+SEM (n=5/group).

Enumeration of antigen-specific IFN-γ secreting cells was done by ELISpot assay. Briefly, spleen cells (at a final cell density of $4\times10^5$/well) were added to 96-well ELISpot plates coated with an anti-IFN-γ antibody (Mabtech Inc., Cincinnati, OH, USA), and incubated in the presence of appropriate antigen-specific stimulant at a concentration of 2 μg/mL for 20 h at 37° C., 5% $CO_2$. For OVA protein-immunized animals, CD8 T cell epitope $OVA_{257-264}$: SIINFEKL (SEQ ID NO: 6) or CD4 T cell epitope $OVA_{323-339}$: ISQAVHAAHAEINEAGR (SEQ ID NO: 7) peptides were used as stimulants. For OVA long peptide-immunized animals, cells were stimulated with peptides corresponding to the CD8 T cell epitope $OVA_{257-264}$: SIINFEKL (SEQ ID NO: 6) or CD4 T cell epitope $OVA_{266-277}$: TEWTSSNVMEER (SEQ ID NO: 8) contained within the long peptide sequence. Meanwhile, Tryp1/PMEL/Trp2 long peptide-immunized animals were stimulated with the individual CD8 epitopes contained within each of the long peptides: $Tryp1_{455-463}$: TAPDNLGYM (SEQ ID NO: 9), $PMEL_{25-33}$: EGPRNQDWL (SEQ ID NO: 10) and $Trp2_{180-188}$: SVYDFFVWL (SEQ ID NO: 11). All peptides were synthesized by JPT Peptide Technologies GmbH. Cells were also incubated without any stimulants to measure background responses. The plates were then incubated, washed and developed according to the manufacturer's instructions. AEC substrate (Becton Dickenson, Franklin Lakes, NJ, USA) was used to visualize the spots. Spots were counted using an automated ELISpot plate reader (BIOSYS, Miami, Florida, USA). In animals immunized with OVA whole protein, an average of 208 and 143 IFNγ+ SIINFEKL (SEQ ID NO: 6)-specific spot-forming cells (SFC)/$10^6$ splenocytes were observed when mice received formulations containing SLA+Poly(I:C) and SLA+CpG, respectively (FIG. 2). All other formulations (containing single adjuvants or SLA in combination with R848, MPLA, QS-21 or $Pam_3CSK_4$) had similarly low levels of SIINFEKL (SEQ ID NO: 6)-specific cells (i.e. <30 IFNγ+ SFC/$10^6$ splenocytes). A similar trend was observed when measuring SFCs reactive to the OVA CD4 epitope, where only mice immunized with OVA formulations containing SLA+Poly(I:C) or SLA+CpG had detectable responses (FIG. 3). The ability of SLA+Poly(I:C) adjuvant combination to enhance CD8 T cell responses was further confirmed using long peptide antigens. These long peptides, consisting of 24-25 amino acids centered around a known CD8 epitope, were formulated alone or with SLA, Poly(I:C) or SLA+Poly(I:C) and administered to animals on Days 0, 7 and 21. As above, spleens were collected and assayed for antigen-specific cells by ELISpot. The OVA long peptide formulations containing single or no adjuvants induced an average of 0-260 IFNγ+ SFC/$10^6$ splenocytes reactive to the SIINFEKL (SEQ ID NO: 6) CD8 epitope, while they were at least 6-fold higher (i.e. 1597 IFNγ+ SFC/$10^6$ splenocytes) in mice immunized with the SLA+Poly(I:C)-adjuvanted formulation (FIG. 9). A similar trend was seen when splenocytes were stimulated with the CD4 epitope (TEWTSSNVMEER, SEQ ID NO: 8) peptide. Separate mice were immunized with long peptide formulations containing 3 epitopes identified from the self-antigens Tryp1, PMEL and Trp2. As with the OVA long peptide, the combination of SLA+Poly(I:C) in the vaccine composition induced higher number of IFNγ+ CD8 T cells than either adjuvant alone (FIG. 10).

Example 4: Testing IgG Production

Figure 4:
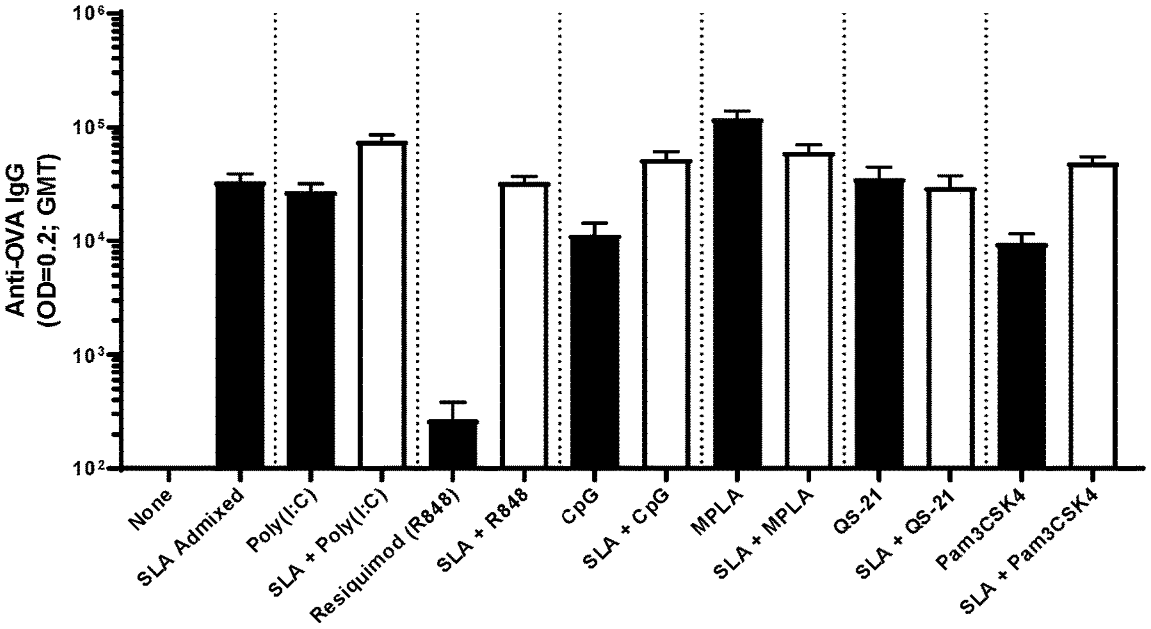
FIG. 4 shows antigen-specific antibody titers in mice. Serum of mice immunized with OVA antigen alone (None) or formulated with SLA archaeosomes, other adjuvants (Poly(I:C), Resiquimod (R848), CpG, MPLA, QS-21, $Pam_3CSK_4$) or SLA in combination with other adjuvants was collected on Day 28 (7 days post $2^{nd}$ immunization by intramuscular route) and analyzed for antigen-specific IgG antibodies by ELISA. Grouped data is presented as geometric mean titer+95% Confidence Interval (n=10/group).
Figure 5:
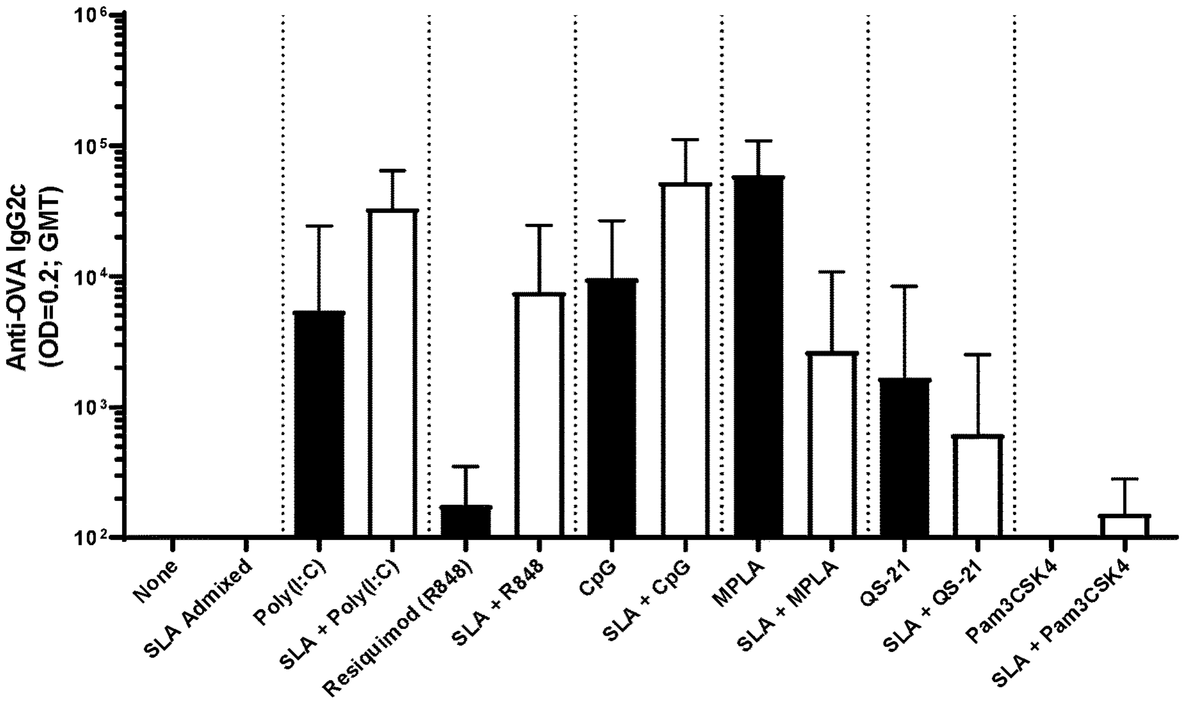
FIG. 5 shows antigen-specific antibody subclass IgG2c titers in mice. Serum of mice immunized with OVA antigen alone (none) or formulated with SLA archaeosomes, other adjuvants (Poly(I:C), Resiquimod (R848), CpG, MPLA, QS-21, $Pam_3CSK_4$) or SLA in combination with other adjuvants was collected on Day 28 (7 days post $2^{nd}$ immunization) and analyzed for antigen-specific IgG2c antibodies by ELISA. Grouped data is presented as geometric mean titer+95% Confidence Interval (n=10/group).
Figure 7:
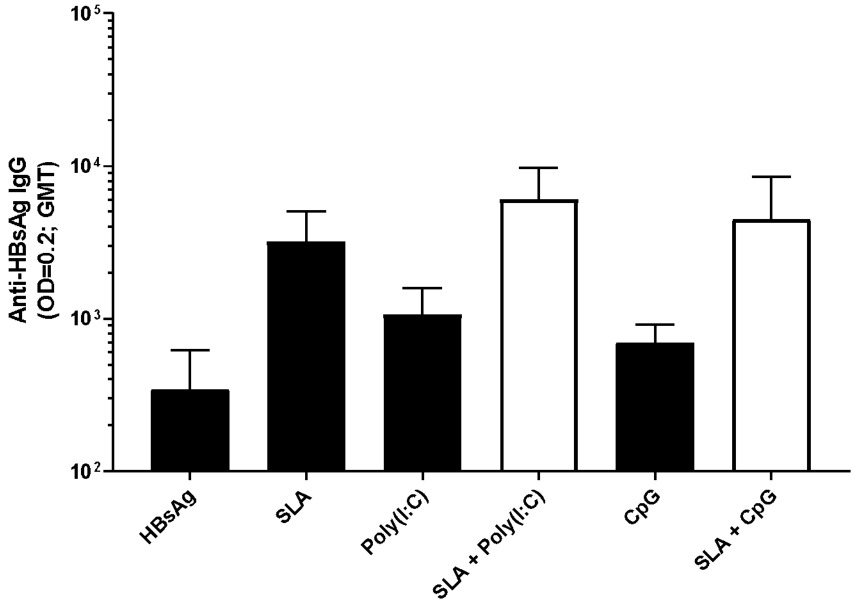
FIG. 7 shows antigen-specific antibody titers in mice pre-boost. Mice were immunized with HBsAg antigen alone or formulated with SLA archaeosomes, Poly(I:C), CpG or SLA in combination with Poly(I:C) or CpG. Serum was collected on Day 20 following a single dose and analyzed for antigen-specific IgG antibodies by ELISA. Grouped data is presented as geometric mean titer+95% Confidence Interval (n=5/group).
Figure 8:
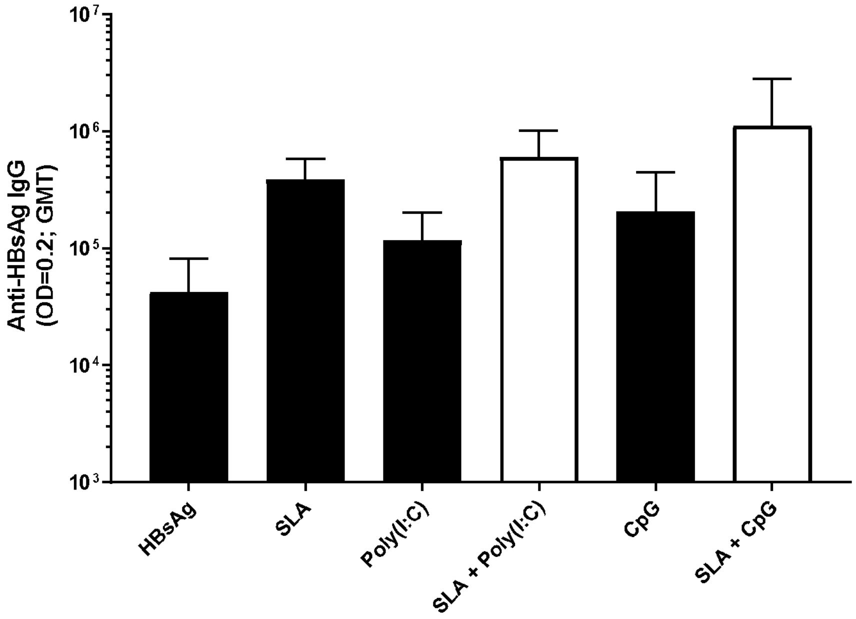
FIG. 8 shows antigen-specific antibody titers in mice post-boost. Mice were immunized with HBsAg antigen alone or formulated with SLA archaeosomes, other adjuvants (Poly(I:C) and CpG) or SLA in combination with other adjuvants on days 0 & 21. On Day 28 (7 days post $2^{nd}$ immunization by intramuscular route) serum was collected and levels of antigen-specific IgG antibodies measured by ELISA. Grouped data is presented as geometric mean titer+95% Confidence Interval (n=5/group).

The levels of anti-OVA or anti-HBsAg antibodies (Abs) in mouse serum were quantified by ELISA using 96-well high-binding ELISA plates (Thermo Fisher Scientific, Waltham, MA, USA) coated overnight at room temperature (RT) with 100 μL of 10 μg/mL OVA (Sigma-Aldrich, St. Louis, MO, USA) in PBS or 1 μg/mL HBsAg (Fitzgerald Industries International) in 16 mM sodium carbonate/34 mM sodium bicarbonate buffer, pH 9.6 (Sigma-Aldrich). Plates were washed five times with PBS/0.05% Tween® 20 (PBS-T; Sigma-Aldrich), and then blocked for 1 hour at 37° C. with 200 μL 10% fetal bovine serum (Thermo Fisher Scientific) in PBS or carbonate/bicarbonate buffer for OVA and HBsAg, respectively. After the plates were washed five times with PBS-T, 3.162-fold serially diluted samples in PBS-T with 10% fetal bovine serum were added in 100 μL volumes and incubated for 1 hour at 37° C. After five washes with PBS/0.05% Tween® 20 (Sigma-Aldrich), 100 μL of goat anti-mouse IgG or IgG2c-HRP (1:4000, Southern Biotech, Birmingham, AL USA) was added for 1 hour at 37° C. After five washes with PBS-T, 100 μL/well of the substrate O-phenylenediamine dihydrochloride (OPD, Sigma-Aldrich) diluted in 0.05 M citrate buffer (pH 5.0) was added. Plates were developed for 30 minutes at RT in the dark. The reaction was stopped with 50 μL/well of 4N $H_2SO_4$. Bound IgG Abs were detected spectrophotometrically at 450 nm. Titers for IgG in serum were defined as the dilution that resulted in an absorbance value (OD 450) of 0.2 and were calculated using Xlfit® software (ID Business Solutions, Guildford, UK). In OVA-immunized mice, anti-OVA IgG titers were >2-fold higher in animals receiving formulations adjuvanted with SLA+Poly(I:C) as compared to formulations containing SLA or Poly(I:C) alone (FIG. 4). Less pronounced increases in anti-OVA IgG titers were also seen in animals immunized with SLA+CpG or SLA+$Pam_3CSK_4$ as compared to the single adjuvant formulations, while the combination of SLA with MPLA led to a decrease in titers compared to MPLA alone. When looking at the IgG2c subtype, the inclusion of Poly(I:C) with SLA in the vaccine composition led to an IgG titer of 33,533 vs. 5420 and 100 (limit of detection) in Poly(I:C) and SLA-adjuvanted formulations, respectively (FIG. 5). Similar trends were observed in HBsAg-immunized mice following either one (FIG. 7) or two (FIG. 8) vaccine doses. Vaccine compositions containing SLA+Poly(I:C) or SLA+CpG induced 1.5-3-fold higher anti-HbsAg IgG titers than when only a single adjuvant was used.

Example 5: Anti-Tumor Activity of OVA SLP Vaccine Formulations in a Therapeutic B16-OVA Tumor Challenge Model To evaluate the potential benefit of SLA+Poly(I:C) as an adjuvant combination in an synthetic long peptide (SLP) vaccine for oncology applications, various vaccine formulations were evaluated in the aggressive B16-OVA melanoma tumor model.

SLA archaeosomes were generated as described in Example 1. Poly(I:C) was purchased from InvivoGen (San Diego, CA, USA) and prepared according to manufacturer's instructions at a concentration of 3 mg/mL and stored at −20° C. until used. The OVA SLP (amino acids 253-277: LEQLESIINFEKLTEWTSSNVMEER) was synthesized by JPT Peptide Technologies GmbH (Berlin, Germany). Based on its theoretical isoelectric point of 4, it was dissolved in slightly alkaline solution (PBS/0.1 M NaOH) at a concentration of 4.4 mg/mL and stored at −20° C. until used.

6-8 week old female C57BL/6 mice were obtained from Charles River Laboratories (Saint-Constant, QC, Canada). On the day of immunization, vaccine formulations were prepared by first mixing the required volume of PBS vehicle and adjuvants (empty pre-formed SLA archaeosomes and/or Poly(I:C)) and briefly vortexing. Thereafter, OVA SLP was added and briefly vortexed. The final concentrations of SLA, Poly(I:C), and OVA long peptide in the injected formulations were 20, 1, and 0.6 mg/mL, respectively. Mice (n=5-10/group) were immunized by intramuscular (i.m.) injection (50 μL) into the left tibialis anterior (T.A.) muscle. Adjuvant (1 mg SLA; 50 μg Poly(I:C)) and antigen (30 μg peptide) dose levels were based on data from previous studies conducted in our laboratory.

Figure 11:
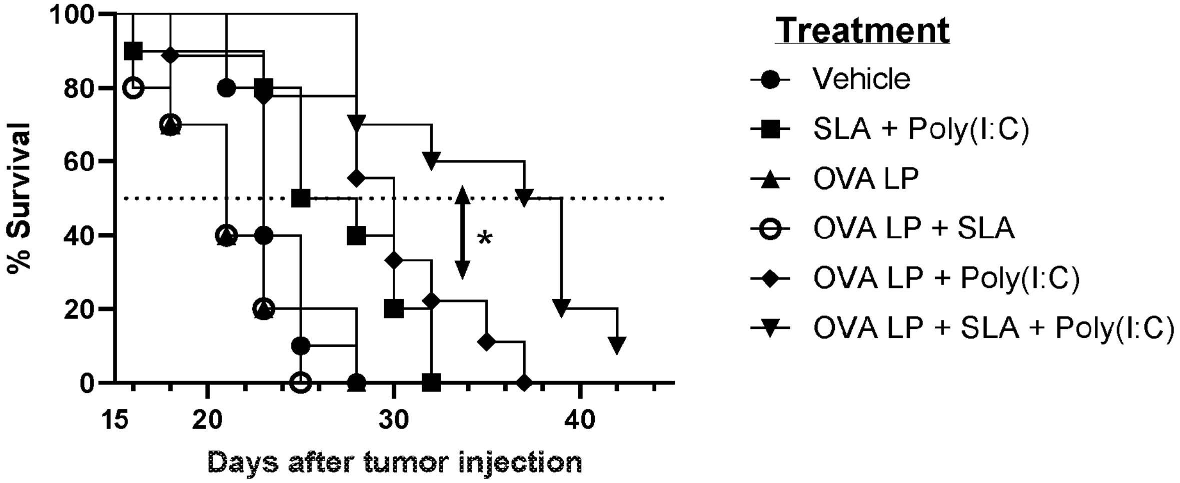
FIG. 11 shows survival of mice vaccinated with OVA synthetic long peptide (SLP) vaccine formulations in a B16-OVA tumor model.

Therapeutic Tumor Challenge Model: B16F0-OVA (expressing plasmid-derived full length OVA) cells, B16 melanoma cells engineered to express ovalbumin protein, were obtained from Dr. Edith Lord (University of Rochester, Rochester, NY, USA) and cultured in R10 media (RPMI containing 10% fetal bovine serum (FBS), 1% penicillin/streptomycin, 1% glutamine, and 55 μM 2-Mercaptoethanol (all from Thermo Fisher Scientific)). Solid tumors were induced with subcutaneous (s.c.) injection of $5\times10^5$ B16-OVA cells in a volume of 100 μL into the lower dorsal area of C57BL/6 mice (n=10/group). Mice were immunized i.m. with OVA SLP (30 μg) with or without adjuvant on days 3, 10, and 17. An adjuvant alone control group received SLA+Poly(I:C) without OVA SLP to determine any potential impact of activation of the innate immune system by the adjuvants on tumor growth. From day 8 onwards, diametrically perpendicular measurements of tumor size (width and length) were measured 2-3 times per week using Digimatic Digital calipers (Mitutoyo 500196, Aurora, IL, USA). An approximation of tumor volume, expressed in $mm^3$, was calculated by multiplication of length×width×width/2. Animals were monitored throughout the duration of the study. Mice were euthanized when they achieved one of the following humane endpoints: (1) the tumor volume exceeded 2000 $mm^3$, (2) ulcerated bleeding tumor, and (3) mice showed signs of clinical illness (e.g., ruffled fur, very little activity, hunched posture, eyes squeezed shut, very sickly). As this was a therapeutic tumor model, only mice that had measurable tumors (>100 mm3) at any time-point prior to the final vaccination dose were included in the analysis. Results are shown in FIG. 11 and Table 4. Statistical significance of difference for OVA SLP+SLA+Poly(I:C) vs. OVA SLP+Poly(I:C): * $p<0.05$ by Mantel-Cox test. There was no significant difference in survival between groups of mice which received vehicle, OVA SLP alone, or OVA SLP+SLA (median survival of 21-23 days).

Meanwhile, a very modest increase (median survival of 26.5 days; $p<0.05$ vs. vehicle alone group) was observed following administration of SLA+Poly(I:C) without any antigen. The delay in tumor growth with the adjuvant control is consistent with previous studies showing that Poly(I:C) when administered alone can activate natural killer cells and suppress tumor growth in a similar B16 melanoma model [Miyake et al, 2009], while SLA has been shown to have inherent immunostimulatory effects [Akache et al, 2018]. Median survival was further extended in animals that received either of the two formulations shown to generate the strongest cytolytic activity, namely OVA SLP+Poly(I:C) and OVA SLP+SLA+Poly(I:C) (median survival of 30 and 38 days, respectively).

Figure 12:
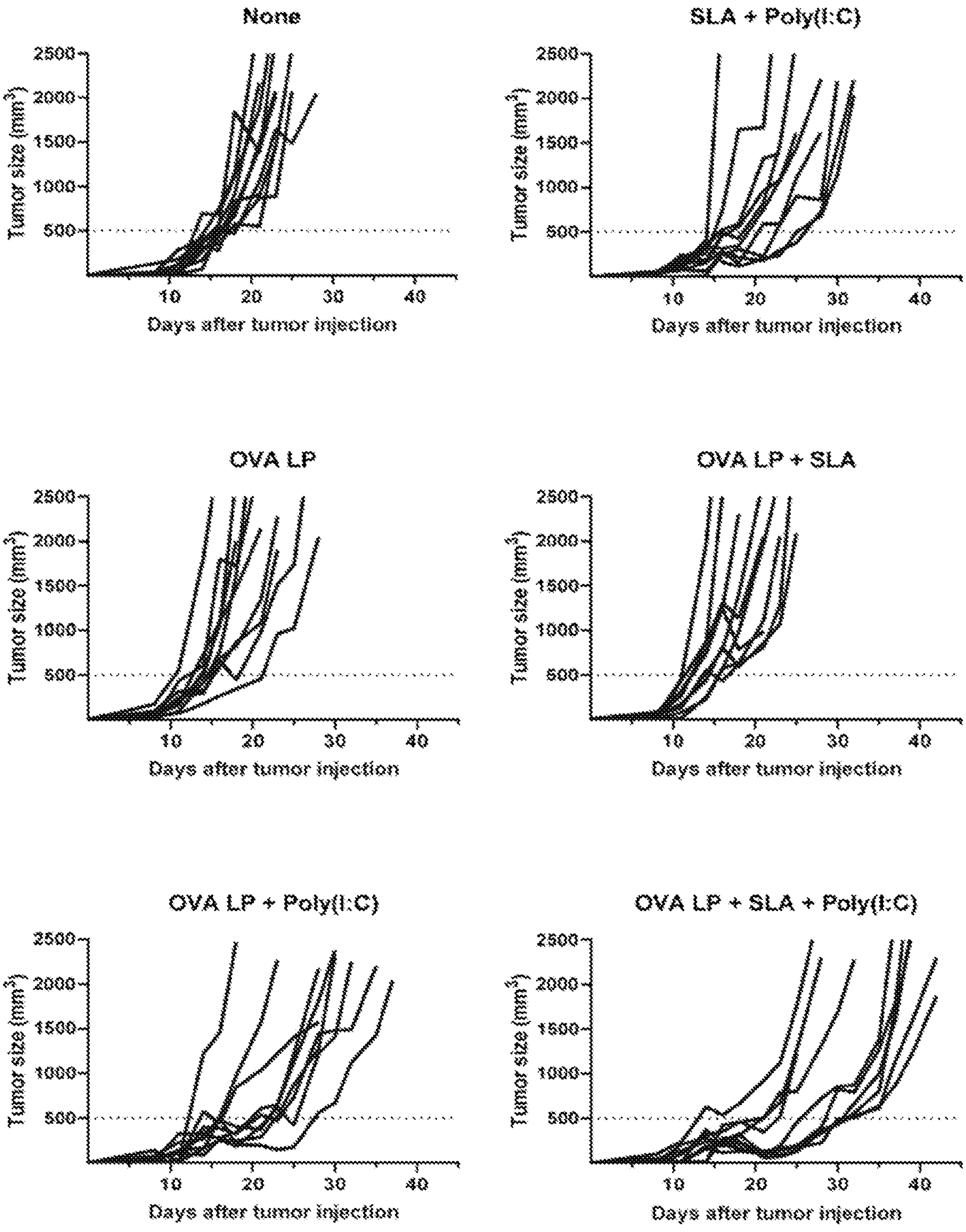
FIG. 12 shows the kinetics of B16-OVA tumor growth in individual C57BL/6 mice (n=10/group) injected s.c. with $5\times10^5$ B16-OVA cells on day 0 and immunized i.m. with OVA SLP (30 μg) with or without adjuvant on days 3, 10, and 17.

The activity of these formulations is further confirmed when directly measuring tumor growth, whereby slowest tumor growth was observed in mice receiving OVA SLP in combination with SLA+Poly(I:C) (FIG. 12). The use of SLA+Poly(I:C) as a combination adjuvant with OVA SLP gave significantly longer survival than was obtained with either the adjuvants alone (i.e., SLA+Poly(I:C) without SLP; $p<0.01$) or OVA SLP in combination with Poly(I:C) or SLA ($p<0.05$; FIG. 11). These results suggest that the ability of the SLA+Poly(I:C) adjuvant combination to induce strong CD8+ functional T cells translates into slower tumor growth and extended survival in a vigorous murine tumor model.

TABLE 4

Median survival of B16-OVA challenged mice.

| Vaccine Treatment | Median Survival (Days) |
|---|---|
| Vehicle | 23 |
| Sulfated Lactosyl Archaeol (SLA) + Poly (I:C) (No Antigen) | 26.5 |
| Ovalbumin synthetic long peptide (OVA SLP) | 21 |
| OVA SLP + SLA | 21 |
| OVA SLP + Poly (I:C) | 30 |
| OVA SLP + SLA + Poly (I:C) | 38 |

Figure 13:
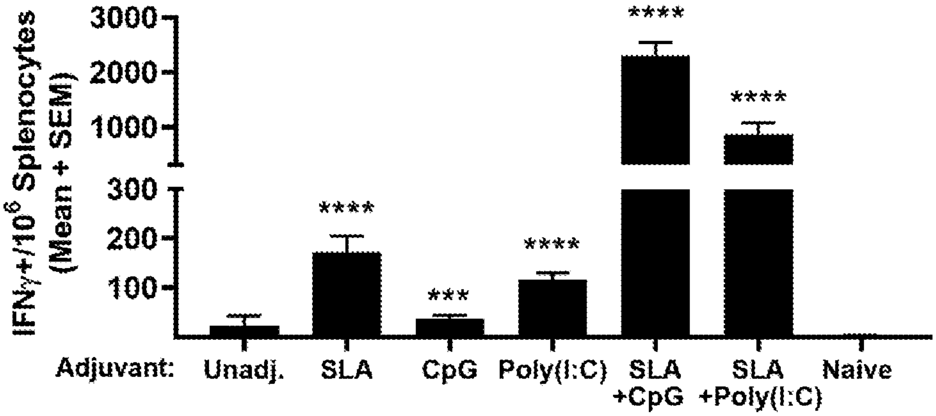
FIG. 13 shows SARS-CoV-2 Spike-specific cellular responses as determined by ELISpot assay. C57BL/6 mice were immunized i.m. with 1 μg of SARS-CoV-2 spike protein (SmT1) alone or with SLA, CpG and Poly(I:C) either alone or in combination on Days 0 and 21. Splenocytes were harvested on day 28 and analyzed by IFN-$\gamma^+$ ELISpot (n 10/group) when stimulated by spike peptide pools Or media alone.
Figure 14:
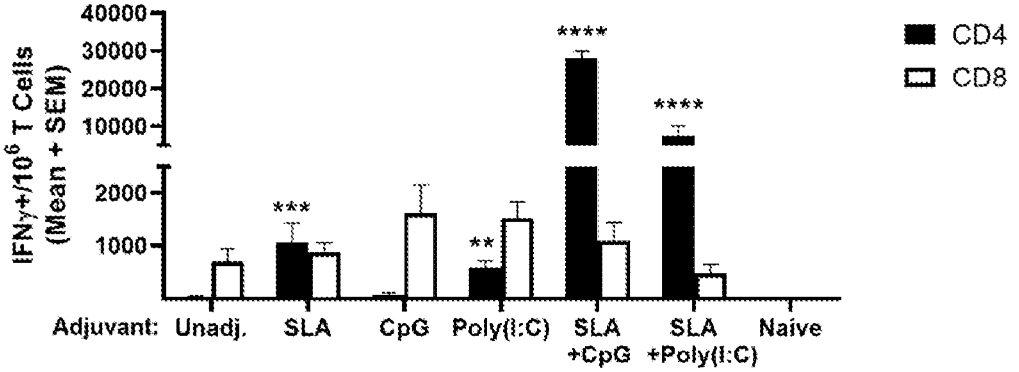
FIG. 14 shows SARS-CoV-2 Spike-specific CD4+ and CD8+ cellular responses as determined by intracellular cytokine staining (ICCS). C57BL/6 mice were immunized i.m. with 1 μg of a recombinant SARS-CoV-2 spike protein (SmT1) alone or with SLA, CpG and Poly(I:C) either alone or in combination on Days 0 and 21. Splenocytes were harvested on day 28 and analyzed by IEGGS (n=5/group) when stimulated by spike peptide pools or media alone.

Example 6: Comparison of Immunogenicity of SARS-CoV-2 Spike Protein Antigen SmT1 with TLR Agonist-Based Adjuvants or SLA/TLR Agonist Combinations Mice (n=10 per group) were immunized on Days 0 and 21 with 1 μg of a resistin-trimerized spike antigen (SmT1) (Akache et al, 2021) alone or adjuvanted with SLA, CpG, Poly(I:C), SLA+CpG or SLA+Poly(I:C). A suboptimal dose of 1 μg antigen was selected to better allow detection of potential synergy between adjuvants. Splenocytes collected on Day 28 were evaluated by IFN-γ ELISpot and intracellular cytokine staining (ICCS) to characterize the antigen-specific cellular responses induced by these vaccine formulations. While all adjuvants induced significantly higher levels of cellular responses than an antigen alone formulation as measured by ELISpot (FIG. 13), the combination adjuvant formulations induced the highest levels of IFN-$\gamma^+$ SFCs with SmT1 adjuvanted with SLA+CpG and SLA+Poly(I:C) inducing an average of 2,308 and 868 IFN-$\gamma^+$ SFCs/$10^6$ splenocytes, respectively. The levels in mice immunized with the SLA+CpG-adjuvanted formulation were significantly higher than seen in all other groups ($p<0.05$). ICCS was used to delineate whether the IFN-$\gamma^+$ cells were of the $CD4^+$ or $CD8^+$ T cell subtype. While IFN-$\gamma^+$ $CD8^+$ T cells were seen in all groups, there was no statistically significant difference between the adjuvanted groups and the unadjuvanted SmT1 control (FIG. 14). Conversely, mice treated with SmT1 adjuvanted with SLA+CpG or SLA+Poly(I:C) had significantly higher levels of IFN-$\gamma^+$ $CD4^+$ T cells than those immunized with unadjuvanted SmT1 or with SmT1 adjuvanted with SLA, CpG, or Poly(I:C). The hierarchy between groups mirrored the ELISpot results with the SLA+CpG-adjuvanted formulation inducing an average of 27,938 IFN-$\gamma^+$ cells/$10^6$ $CD4^+$ T cells.

Figure 15:
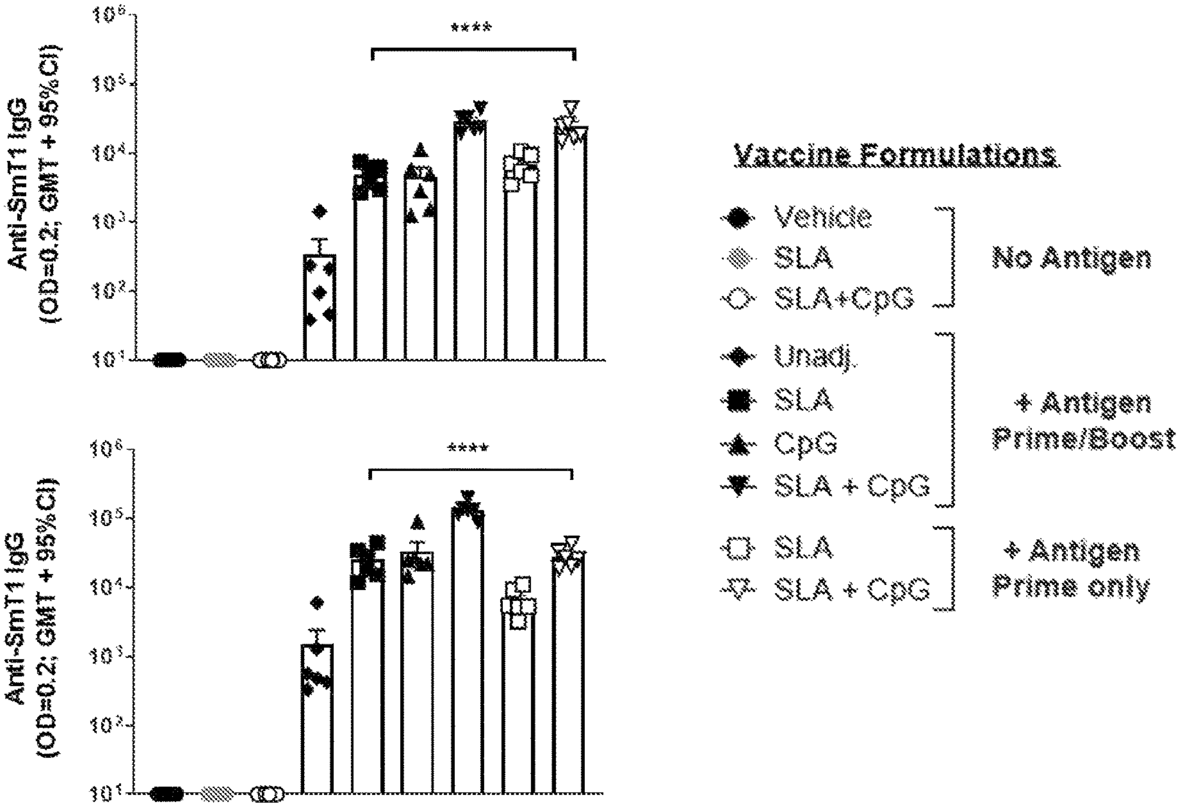
FIG. 15 shows SARS-CoV-2 Spike-specific antibody titers in hamsters. Syrian Golden hamsters were immunized i.m. with 3 μg of SmT1 alone or with SLA, CpG or SLA+CpG on Days 0±21. Serum was collected on Days 21 (upper panel) and 34 (lower panel) and levels of antigen-specific IgG antibodies measured by ELISA. Grouped data is presented as geometric mean titer+95% Confidence Interval (n=6/group).

Example 7: Immunogenicity of SmT1-Based Vaccine Formulations Adjuvanted with SLA, CpG or SLA+CpG in Hamster Model Syrian Golden hamsters (n=6/group) were immunized i.m. with 3 μg of SmT1 alone or with SLA, CpG or SLA+CpG on Days 0±21. Serum was collected on Days 21 (FIG. 15, upper panel) and 34 (1 day prior to viral challenge) (FIG. 15, lower panel) and analyzed by ELISA to determine the antibody titers. Grouped data is presented as geometric mean+95% confidence interval. No antigen-specific antibodies were detected in any of the groups on Day 0 (data not shown), as well as the control groups immunized with vehicle or adjuvant alone at Days 21 and 34 (FIG. 15). Anti-spike IgG titers were observed in all hamsters immunized with antigen alone following a single vaccine dose, GMT (lower & upper 95% CI) of 150 (37 & 605) (FIG. 15, upper panel). The adjuvanted formulations induced significantly higher antigen-specific antibody titers than antigen alone ($P<0.0001$). At Day 34, titers increased fivefold in groups that received a boost immunization at Day 21, while they were virtually unchanged in the groups immunized on Day 0 only. Despite some of the groups only receiving a single prime vaccine dose, titers were still significantly higher in all the groups immunized with the adjuvanted formulations than in the antigen alone group ($p<0.0001$; FIG. 15, lower panel). The prime only vaccine regimens of SmT1 adjuvanted with SLA or SLA+CpG induced GMT of 6,050 and 26,801, respectively, Amongst the groups that received the prime/boost regimens, the SLA+CpG-adjuvanted tbrmulation induced significantly higher titers than the single adjuvant formulations: GMT of 127,989 vs. 22,629-27,430 with SLA or CpG-adjuyanted SmT1 ($p<0.01$).

The preceding examples have been provided to allow a greater understanding of the present disclosure by illustrating specific examples that are in accordance with embodiments of the disclosure. The accompanying claims should not be limited to the specific details provided in the examples. Rather, they should be given the broadest interpretation that is consistent with the collective teaching of the specification and drawings, in consideration of the common general knowledge in the art.

REFERENCES

Agbayani, G., Jia, Y., Akache, B., et al., Mechanistic insight into the induction of cellular immune responses by encapsulated and admixed archaeosome-based vaccine formulations. Human vaccines & immunotherapeutics 2020; 16:2183-2195.

Akache B, Stark F C, Jia Y, et al. Sulfated archaeol glycolipids: Comparison with other immunological adjuvants in mice. PloS One. 2018; 13(12):e0208067.

Akache B, Renner T M, Tran A, et al. Immunogenic and efficacious SARS-CoV-2 vaccine based on resistin-trimerized spike antigen SmT1 and SLA archaeosome adjuvant, *Sci Rep* 11, 21849 (2021).

Aoki T, Poulter C D, Archaebacterial isoprenoids. Synthesis of 2,3-di-O-phytanyl-sn-glycerol and its 1,2-isomer. The Journal of Organic Chemistry. 1985; 50:5634-5636.

Annunziato F, Romagnani C, Romagnani S. The 3 types of innate and adaptive cell-mediated effector immunity. The Journal of Allergy and Clinical Immunology. 2015; 235(3):626-635.

Barber D L, Wherry E J, Ahmed R. Cutting edge: rapid in vivo killing by memory CD8 T cells. J. Immunol. 2003 Jul. 1; 171(1):27-31.

Benvegnu T, Lemiègre L, Cammas-Marion S. New generation of liposomes called archaeosomes based on natural or synthetic archaeal lipids as innovative formulations for drug delivery. Recent Pat Drug Deliv Formul. 2009 November; 3(3): 206-20.

Hickie R, Balsevich J, Ramirez-Erosa I, Dunlop D, Bishop G, Deibert L, Arnison P, "Saponin extract from *saponaria* spp. and uses thereof", US patent publication no. US20110230430A1, 22 Sep. 2011.

Jia Y, Akache B, Deschatelets L, et al. A comparison of the immune responses induced by antigens in three different archaeosome-based vaccine formulations. Int J Pharm. 2019 Apr. 20; 561:187-196.

Martins K A O, Bavari S, Salazar A M. Vaccine adjuvant uses of poly-IC and derivatives, Expert Review of Vaccines, 2015, 14:3, 447-459.

TABLE 5

Sequences

| Name | Sequence | Description |
|---|---|---|
| SEQ ID NO: 1 | LEQLESIINFEKLTEWTSSNVMEER | $OVA_{253-277}$ |
| SEQ ID NO: 2 | VTNTEMFVTAPDNLGYMYEVQWPG | $Tryp1_{447-470}$ |
| SEQ ID NO: 3 | ALLAVGALEGPRNQDWLGVPRQLVT | $PMEL_{17-41}$ |
| SEQ ID NO: 4 | TQPQIANCSVYDFFVWLHYYSVRDT | $Trp2_{172-196}$ |
| SEQ ID NO: 5 | IPQSLDSWWTSL | HbsAg CD8 epitope |
| SEQ ID NO: 6 | SIINFEKL | CD8 T cell epitope $OVA_{257-264}$ |
| SEQ ID NO: 7 | ISQAVHAAHAEINEAGR | CD4 T cell epitope $OVA_{323-339}$ |
| SEQ ID NO: 8 | TEWTSSNVMEER | CD4 T cell epitope $OVA_{266-277}$ |
| SEQ ID NO: 9 | TAPDNLGYM | $Tryp1_{455-463}$ |
| SEQ ID NO: 10 | EGPRNQDWL | $PMEL_{25-33}$ |
| SEQ ID NO: 11 | SVYDFFVWL | $Trp2_{180-188}$ |

McCluskie M J, Deschatelets L, Krishnan L. Sulfated archaeal glycolipid archaeosomes as a safe and effective vaccine adjuvant for induction of cell-mediated immunity. Hum Vaccin Immunother. 2017; 13(12): 2772-2779.

Miyake, T.; Kumagai, Y.; Kato, H.; Guo, Z.; Matsushita, K.; Satoh, T.; Kawagoe, T.; Kumar, H.; Jang, M. H.; Kawai, T.; et al. Poly I:C-Induced Activation of NK Cells by CD8 Alpha+ Dendritic Cells via the IPS-1 and TRIF-Dependent Pathways. J. Immunol. Baltim. Md 1950 2009, 183, 2522-2528.

Moses T, Papadopoulou K K, Osbourn A. Metabolic and functional diversity of saponins, biosynthetic intermediates and semi-synthetic derivatives. Crit Rev Biochem Mol Biol. 2014; 49(6):439-462.

Ragupathi G, Gardner J R, Livingston P O, et al. Natural and synthetic saponin adjuvant QS-21 for vaccines against cancer. Expert Rev Vaccines. 2011; 10(4):463-470.

Stark, F. C., Akache, B., Ponce, A., et al., Archaeal glycolipid adjuvanted vaccines induce strong influenza-specific immune responses through direct immunization in young and aged mice or through passive maternal immunization. Vaccine 2019; 37:7108-7116.

Whitfield D M, Sprott G D, Krishnan L, inventors; National Research Council of Canada, assignee. Sulfated-glycolipids as adjuvants for vaccines. International patent publication WO 2016/004512 A1. Jan. 14, 2016.

Whitfield D M, Yu S H, Dicaire C J, et al. Development of new glycosylation methodologies for the synthesis of archaeal-derived glycolipid adjuvants. Carbohydr Res. 2010 Jan. 26; 345(2):214-29.

What is claimed is:

1. An adjuvant composition comprising:

a glycoarchaeol or a pharmaceutically acceptable salt thereof, and at least one immunostimulant selected from a Toll-like receptor (TLR) agonist or a pharmaceutically acceptable salt thereof, wherein the TLR agonist is a TLR3 agonist or TLR9 agonist, wherein the glycoarchaeol is a charged isoprenoid glycolipid comprising a sulfated saccharide group covalently linked to a free sn-1 hydroxyl group of a glycerol backbone of an archaeol core moiety via a beta linkage.

2. The adjuvant composition of claim 1, wherein the archaeol core moiety is 2,3-bis(((3,7,11)-3,7,11,15-tetramethylhexadecyl)oxy)propan-1-ol.

3. The adjuvant composition of claim 1, wherein the sulfated saccharide group is a sulfated disaccharide or trisaccharide.

4. The adjuvant composition of claim 1, wherein the sulfated saccharide group is 6'-sulfate-β-D-Galp-(1,4)-β-D-Glcp.

5. The adjuvant composition of claim 1, wherein the glycoarchaeol is 2,3 bis[(3,7,11)-3,7,11,15-tetramethylhexadecyloxy]propan-1-yl 4-O-(6-O-sulfo-β-D-galactopyranosyl)-β-D-glucopyranoside.

6. The adjuvant composition of claim 1, wherein the glycoarchaeol is of Formula I:

I

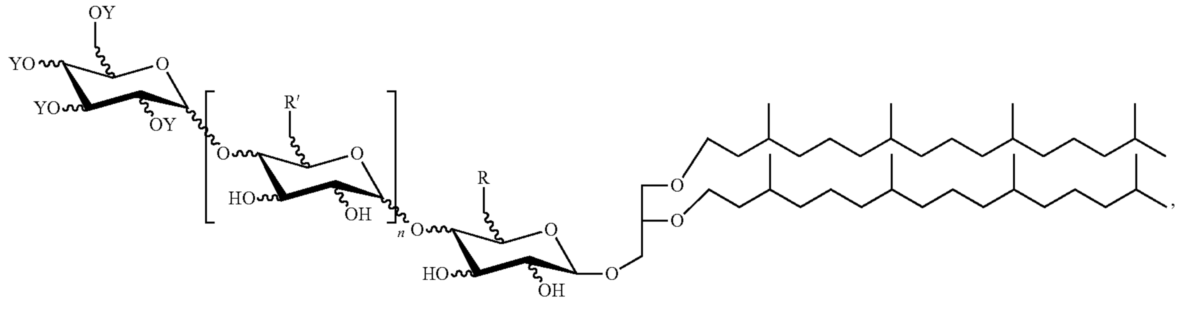

wherein n is 0 or 1;

R and R' are independently hydrogen or hydroxyl; and

Y is hydrogen or a sulfate group, and at least one Y is a sulfate group.

7. The adjuvant composition of claim 1, wherein the glycoarchaeol is of the structure:

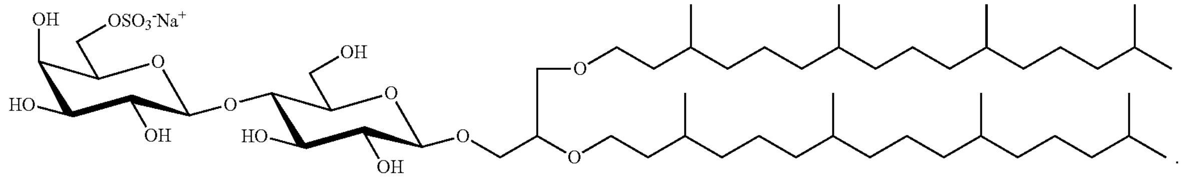

8. The adjuvant composition of claim 1, wherein the glycoarchaeol or the pharmaceutically acceptable salt thereof is comprised within an archaeosome.

9. The adjuvant composition of claim 8, wherein the archaeosome further comprises at least one additional lipid, and wherein the at least one additional lipid is a neutrally charged or uncharged glycolipid.

10. The adjuvant composition of claim 9, wherein the at least one additional lipid is a lactosylarchaeol, a rhamnosyllactosylarchaeol, a triglucosylarchaeol, or a combination of any two or more thereof.

11. The adjuvant composition of claim 9, wherein the mol % ratio of the glycoarchaeol or the pharmaceutically acceptable salt thereof to the at least one additional lipid is from 30:70 to about 50:50.

12. The adjuvant composition of claim 1, wherein the at least one immunostimulant is a TLR3 agonist, or a pharmaceutically acceptable salt thereof, wherein the TLR3 agonist is Poly(I:C) or a pharmaceutically acceptable salt thereof.

13. An immunogenic composition comprising an antigen and the adjuvant composition of claim 1.

14. The immunogenic composition of claim 13, wherein the antigen is a peptide, protein, or virus-like particle.

15. A method of inducing an immune response in a subject, the method comprising administering to the subject the immunogenic composition of claim 14.

16. The method of claim 15, wherein the immune response comprises a cell-mediated response and a humoral response, wherein the humoral response comprises an IgG response, and wherein the cell-mediated response comprises at least one of a CD4+ response, a CD8+ response, a cytotoxic response, and production of at least one cytokine.

17. The adjuvant composition of claim 1, wherein the at least one immunostimulant is a TLR9 agonist, or a pharmaceutically acceptable salt thereof, wherein the TLR9 agonist is an oligonucleotide comprising one or more CpG motifs.

18. The immunogenic composition of claim 13, which is a vaccine composition.

19. The immunogenic composition of claim 18, which is prepared by admixing the glycoarchaeol or the pharmaceutically acceptable salt thereof, the at least one immunostimulant, and the antigen.

* * * * *